US010408837B2

(12) United States Patent
Wang et al.

(10) Patent No.: US 10,408,837 B2
(45) Date of Patent: Sep. 10, 2019

(54) PEPTIDE SUBSTRATES RECOGNIZABLE BY TYPE E BOTULINUM NEUROTOXIN

(71) Applicant: The United States of America, as represented by the Secretary, Department of Health & Human Services, Rockville, MD (US)

(72) Inventors: Dongxia Wang, Duluth, GA (US); Suzanne R. Kalb, Atlanta, GA (US); John R. Barr, Suwanee, GA (US)

(73) Assignee: The United States of America, as represented by the Secretary, Department of Health & Human Services, Rockville, MD (US)

( * ) Notice: Subject to any disclaimer, the term of this patent is extended or adjusted under 35 U.S.C. 154(b) by 0 days.

(21) Appl. No.: 15/103,295

(22) PCT Filed: Dec. 9, 2013

(86) PCT No.: PCT/US2013/073885
§ 371 (c)(1),
(2) Date: Jun. 9, 2016

(87) PCT Pub. No.: WO2015/088477
PCT Pub. Date: Jun. 18, 2015

(65) Prior Publication Data
US 2016/0305940 A1    Oct. 20, 2016

(51) Int. Cl.
*C07K 14/00* (2006.01)
*C07K 14/705* (2006.01)
*G01N 33/573* (2006.01)
*G01N 33/569* (2006.01)

(52) U.S. Cl.
CPC ......... *G01N 33/573* (2013.01); *C07K 14/001* (2013.01); *C07K 14/705* (2013.01); *G01N 33/56911* (2013.01); *G01N 2333/952* (2013.01); *G01N 2469/10* (2013.01)

(58) Field of Classification Search
None
See application file for complete search history.

(56) References Cited

U.S. PATENT DOCUMENTS

| | | | | |
|---|---|---|---|---|
| 5,962,637 | A * | 10/1999 | Shone | C07K 16/28 435/7.1 |
| 6,043,042 | A * | 3/2000 | Shone | C07K 16/28 435/34 |
| 6,337,386 | B1 * | 1/2002 | Shone | C07K 16/28 435/7.1 |
| 6,803,475 | B2 | 10/2004 | Wipf | |
| 7,160,982 | B2 * | 1/2007 | Roques | C07K 14/705 435/4 |
| 7,611,856 | B2 * | 11/2009 | Schmidt | G01N 33/6848 435/7.72 |
| 7,632,917 | B2 * | 12/2009 | Kincaid | C07K 14/705 424/239.1 |
| 7,670,796 | B2 * | 3/2010 | Shone | C12Q 1/37 435/23 |
| 7,875,436 | B2 * | 1/2011 | Fournie-Zaluski | C07K 5/0812 435/24 |
| 8,137,924 | B2 * | 3/2012 | Chapman | C07K 14/43595 435/7.32 |
| 8,198,034 | B2 * | 6/2012 | Fernandez-Salas | C07K 16/1282 435/325 |
| 8,455,203 | B2 * | 6/2013 | Wang | C12Q 1/37 435/325 |
| 8,455,213 | B2 * | 6/2013 | Zhu | C12N 5/0618 435/25 |
| 8,455,247 | B2 * | 6/2013 | Zhu | C12N 5/0618 435/325 |
| 8,476,068 | B2 * | 7/2013 | Zhu | C12N 5/0618 435/325 |
| 8,871,496 | B1 * | 10/2014 | Sommer | C12Q 1/37 422/68.1 |
| 8,999,649 | B2 * | 4/2015 | Chapman | C07K 14/43595 435/6.15 |
| 9,005,911 | B2 * | 4/2015 | Kincaid | C07K 14/705 424/239.1 |
| 9,249,216 | B2 * | 2/2016 | Fernandez-Salas | C07K 16/1282 |
| 2006/0024763 | A1 * | 2/2006 | Schmidt | C12Q 1/37 435/7.5 |
| 2009/0208993 | A1 * | 8/2009 | Fournie-Zaluski | C07K 5/0812 435/24 |
| 2010/0281003 | A1 * | 11/2010 | Jochim | G06F 19/16 707/692 |

(Continued)

FOREIGN PATENT DOCUMENTS

WO    WO 2008/036060 A2    3/2008
WO    WO-2011018665 A1 *   2/2011   ........... C07K 14/705

(Continued)

OTHER PUBLICATIONS

Dong et al, Bioorganic & Medicinal Chemistry. 2015, 23:3667-3673. available online Apr. 10, 2015 (Year: 2015).*
Kalb et al, PLoSOne. Apr. 2009, 4/4:e5355, 8 pages. published Apr. 28, 2009. (Year: 2009).*
Kalb et al, PLoSOne. Aug. 2010, 5/8:e12237, 11 pages. published Aug. 17, 2010 (Year: 2010).*

(Continued)

*Primary Examiner* — Nita M. Minnifield
(74) *Attorney, Agent, or Firm* — Locke Lord LLP; Christopher J. Capelli; Nicholas J. DiCeglie, Jr.

(57) ABSTRACT

The present invention relates to peptide substrates selectively recognized by botulinum toxin type A, BoNT/E, and their uses, in particular for carrying out methods for detecting, identifying and/or diagnosing botulinum toxin type E.

8 Claims, 5 Drawing Sheets
Specification includes a Sequence Listing.

(56) References Cited

U.S. PATENT DOCUMENTS

| | | | |
|---|---|---|---|
| 2011/0038892 A1* | 2/2011 | Davletov | C07K 14/705 424/239.1 |
| 2011/0318385 A1* | 12/2011 | Jackson | C07K 14/33 424/239.1 |
| 2015/0038372 A1* | 2/2015 | Sommer | C12Q 1/37 506/11 |
| 2015/0253326 A1* | 9/2015 | Chapman | C07K 14/43595 506/10 |
| 2016/0305940 A1* | 10/2016 | Wang | G01N 33/56911 |
| 2016/0356776 A1* | 12/2016 | Chapman | C07K 14/43595 |
| 2017/0283487 A1* | 10/2017 | Fernandez-Salas | C07K 16/1282 |
| 2018/0045733 A1* | 2/2018 | Eisele | G01N 33/6809 |

FOREIGN PATENT DOCUMENTS

| | | | | |
|---|---|---|---|---|
| WO | WO-2011038892 A1 * | 4/2011 | | A61B 5/0059 |
| WO | WO-2013011055 A1 * | 1/2013 | | C12Q 1/37 |
| WO | WO-2014080206 A1 * | 5/2014 | | C12Q 1/37 |
| WO | WO-2015088477 A1 * | 6/2015 | | G01N 33/56911 |

OTHER PUBLICATIONS

Wang et al. Anal. Chem., 2014. 86:10847-10854. published Oct. 6, 2014 (Year: 2014).*
Wang et al, Analytical Biochemistry, 2015, 468:15-21. Available online Sep. 16, 2014 (Year: 2014).*
Schmidt et al, Analytical Biochemistry, 2001, 296:130-137. published inline: Aug. 6, 2001 (Year: 2001).*
Schmidt et al, Applied and Environmental Microbiology, Jan. 2003, 69/1:297-303. (Year: 2003).*
Schiavo et al., 1992, J. Biol. Chem. 267, 23479-23483.
Roques B.P. 1993, Biochem. Soc. Trans. 21, 678-685.
Chen et al., Apr. 21, 2006; 281(16): 10906-11.
Kautter and Salomon, 1976 J. Assoc. Anal. Chem., 60, 541-545.
Karlin and Altschul 1990, Proc. Natl. Acad. Sci. USA, 87:2264-2268.
Karlin and Altschul 1993, Proc. Natl. Acad. Sci. USA, 90:5873-5877.
Altschul, et al. 1990, J. Mol. Biol. 215:403-410.
Myers and Miller, 1988, CABIOS 4:11-17 (algorithum).
Pearson and Lipman 1988, Proc. Natl., Acad. Sci. USA 85:2444-2448.
Narang, 1983, Tetrahedron 39:3.
Itakura et al., 1984, Annul. Rev. Biochem. 53:323.
Itakura et al., 1984, Science 198:1056.
Ike et al., 1983, Nucleic Acid Res. 11:477.
Arkin and Yourvan, 1992, Porc. Natl., Acad. Sci. USA 89:7811-7815.
Delgrave, et al., 1993, Protein Engineering 6(3):327-331.
S.R. Kalb, et al., International Journal of Mass Spectrometry 2008, 278, 101-108.
S.R. Kalb, et al., The Botulinum J. 2012, 2(2), 119-134.
S.R. Kalb, et al., Anal Biochem 2006, 351, 84-92.
International Search Report as dated Oct. 13, 2014, for PCT/US2013/073885.
Written Opinion of the International Searching Authority as dated Jun. 9, 2016, for PCT/US2013/073885.
Wang D et al: "Optimization of Peptide Substrates for the Sensitive Detection of Type E Botulinum Neurotoxin by the Endopep-MS Assay", Biopolymers, vol. 100, No. 3, Sp. Iss. SI, May 2013 (May 2013), p. 286, XP002726750, & 23rd American Peptide Symposium; Waikoloa, HI, USA; Jun. 22-27, 2013 Abstract P179; p. 286.
Suzanne R. Kalb et al: "Detection, differentiation, and subtyping of botulinum toxins A, B, E, and F by mass spectrometry", The Botulinum J., vol. 2, No. 2, Jan. 1, 2012 (Jan. 1, 2012), p. 119, XP055126928, ISSN: 1754-7318, DOI: 10.1504/TBJ.2012.050194.
Brian H Raphael et al: "Analysis of a unique Clostridium botulinum strain from the Southern hemisphere producing a novel type E botulinum neurotoxin subtype", BMC Microbiology, Biomed Central Ltd, GB, vol. 12, No. 1, Oct. 31, 2012,(Oct. 31, 2012), p. 245, XP021134867, ISSN: 1471-2180, DOI: 10.1186/1471-2180-12-245.

\* cited by examiner

Table 4. Effect of single amino acid mutations on the detection of cleavage of mutated peptide-32 by BoNT/E. The sequence of the peptide-32 is: $I_1I_2I_3G_4N_5L_6G_7N_8E_9I_{10}D_{11}T_{12}Q_{13}N_{14}R_{15}Q_{16}I_{17}D_{18}R_{19}I_{20}M_{21}E_{22}K_{23}A_{24}D_{25}S_{26}N_{27}K_{28}R_{29}$ (X:norleucine)

| Group | Single substitution | Relative product (%) |
|---|---|---|
| 1 | I1F, I2F, I3F, N5K, Q13R, Q13K, E22A, D25K, D25R, S26K, S26R, N27K | >300 |
| 2 | I1A, I2A, G4K, N5A, N5G, N8Q, I20K, E22G, E22I, E22F, N27R | 150 - 300 |
| 3 | I1P, G4A, G4D, N5D, N5Q, N8A, Q13A, I17F, M21X, D25A | 100 - 150 |
| 4 | no mutation (Peptide-32) | 100 |
| 5 | I2P, I3A, I3P, G4R, N8E, T12S, Q13E, Q13N, N14A, N14K, N14Q, R15K, Q16K, E22D, K23R, A24G, A24I, A24V, D25E, S26A, S26T, N27A, K28R | 50 - 100 |
| 6 | G4I, L6F, G7K, E9A, E9K, E9N, I10A, I10K, D11A, D11E, D11K, T12A, Q16E, D18A, D18N, R19A, R19K, M21A, M21S, E22K, K23A, K28A | 10 - 50 |
| 7 | L6A, L6P, G7A, G7D, I10D, D11N, N14D, R15A, Q16A, I17A, I17D, I17P, D18E, D18K, I20A | <10 |

FIG. 2

SEQUENCE LISTING

<160> NUMBER OF SEQ ID NOS: 71

<210> SEQ ID NO 1
<211> LENGTH: 206
<212> TYPE: PRT
<213> ORGANISM: Mus musculus

<400> SEQUENCE: 1

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 2
<211> LENGTH: 35
<212> TYPE: PRT
<213> ORGANISM: Mus musculus

<400> SEQUENCE: 2

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys Ala Asp Ser
            20                  25                  30

Asn Lys Thr
        35

<210> SEQ ID NO 3
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(1)
<223> OTHER INFORMATION: /replace="1-Nal" or "2-Nal" or "Phe" or "Tyr"

```
        or "Ile" or "Leu" or "Nle" or "Ala" or "any other hydrophobic
        amino acid residue"
<220> FEATURE:
<221> NAME/KEY: VARIANT
<222> LOCATION: (2)..(2)
<223> OTHER INFORMATION: /replace="1-Nal" or "2-Nal" or "Phe" or "Tyr"
        or "Ile" or "Leu" or "Nle" or "Ala" or "any other hydrophobic
        amino acid residue"
<220> FEATURE:
<221> NAME/KEY: VARIANT
<222> LOCATION: (3)..(3)
<223> OTHER INFORMATION: /replace="1-Nal" or "2-Nal" or "Phe" or "Tyr"
        or "Ile" or "Leu" or "Nle" or "Ala" or "any other hydrophobic
        amino acid residue"
<220> FEATURE:
<221> NAME/KEY: VARIANT
<222> LOCATION: (4)..(4)
<223> OTHER INFORMATION: /replace="Gly"
<220> FEATURE:
<221> NAME/KEY: VARIANT
<222> LOCATION: (5)..(5)
<223> OTHER INFORMATION: /replace="Lys" or "Ala" or "Gly"
<220> FEATURE:
<221> NAME/KEY: VARIANT
<222> LOCATION: (7)..(13)
<223> OTHER INFORMATION: /replace=" "
<220> FEATURE:
<221> NAME/KEY: misc_feature
<222> LOCATION: (7)..(13)
<223> OTHER INFORMATION: /note="This region may or may not be present in
        its entirety"
<220> FEATURE:
<221> NAME/KEY: VARIANT
<222> LOCATION: (15)..(15)
<223> OTHER INFORMATION: /replace="Gln"
<220> FEATURE:
<221> NAME/KEY: VARIANT
<222> LOCATION: (20)..(20)
<223> OTHER INFORMATION: /replace="Arg" or "Lys" or "any other
        positively charged residue"
<220> FEATURE:
<221> NAME/KEY: VARIANT
<222> LOCATION: (24)..(24)
<223> OTHER INFORMATION: /replace="Phe" or "Lys" or "Arg"
<220> FEATURE:
<221> NAME/KEY: VARIANT
<222> LOCATION: (26)..(26)
<223> OTHER INFORMATION: /replace="homoArg" or "Cit" or "Orn"
<220> FEATURE:
<221> NAME/KEY: VARIANT
<222> LOCATION: (28)..(28)
<223> OTHER INFORMATION: /replace="Nle"
<220> FEATURE:
<221> NAME/KEY: VARIANT
<222> LOCATION: (29)..(29)
<223> OTHER INFORMATION: /replace="Phe" or "Gly" or "Ile"
<220> FEATURE:
<221> NAME/KEY: VARIANT
<222> LOCATION: (32)..(32)
<223> OTHER INFORMATION: /replace="Lys" or "Arg" or "any other
        positively charged residue"
<220> FEATURE:
<221> NAME/KEY: VARIANT
<222> LOCATION: (33)..(33)
<223> OTHER INFORMATION: /replace="Lys" or "Arg" or "any other
        positively charged residue"
<220> FEATURE:
<221> NAME/KEY: VARIANT
<222> LOCATION: (34)..(34)
<223> OTHER INFORMATION: /replace="Lys" or "Arg" or "any other
        positively charged residue"
<220> FEATURE:
<221> NAME/KEY: VARIANT
<222> LOCATION: (35)..(35)
<223> OTHER INFORMATION: /replace="Arg" or "any other positively
        charged residue"
<220> FEATURE:
<221> NAME/KEY: VARIANT
<222> LOCATION: (36)..(36)
```

```
<223> OTHER INFORMATION: /replace=" "
<220> FEATURE:
<221> NAME/KEY: misc_feature
<222> LOCATION: (1)..(37)
<223> OTHER INFORMATION: /note="Variant residues given in the sequence
      have no preference with respect to those in the annotations
      for variant positions"

<400> SEQUENCE: 3

Trp Trp Trp Ala Asn Leu Arg His Met Ala Leu Asp Met Gly Asn Glu
1               5                   10                  15

Ile Asp Thr Gln Asn Arg Gln Ile Asp Arg Ile Met Ala Lys Ala Asp
            20                  25                  30

Ser Asn Lys Thr Arg
        35

<210> SEQ ID NO 4
<211> LENGTH: 66
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (1)..(14)
<223> OTHER INFORMATION: /replace=" "
<220> FEATURE:
<221> NAME/KEY: misc_feature
<222> LOCATION: (1)..(14)
<223> OTHER INFORMATION: /note="This region may or may not be present in
      its entirety"
<220> FEATURE:
<221> NAME/KEY: VARIANT
<222> LOCATION: (15)..(15)
<223> OTHER INFORMATION: /replace="1-Nal" or "2-Nal" or "Phe" or "Tyr"
      or "Ile" or "Leu" or "Nle" or "Ala" or "any other hydrophobic
      amino acid residue"
<220> FEATURE:
<221> NAME/KEY: VARIANT
<222> LOCATION: (16)..(16)
<223> OTHER INFORMATION: /replace="1-Nal" or "2-Nal" or "Phe" or "Tyr"
      or "Ile" or "Leu" or "Nle" or "Ala" or "any other hydrophobic
      amino acid residue"
<220> FEATURE:
<221> NAME/KEY: VARIANT
<222> LOCATION: (17)..(17)
<223> OTHER INFORMATION: /replace="1-Nal" or "2-Nal" or "Phe" or "Tyr"
      or "Ile" or "Leu" or "Nle" or "Ala" or "any other hydrophobic
      amino acid residue"
<220> FEATURE:
<221> NAME/KEY: VARIANT
<222> LOCATION: (18)..(18)
<223> OTHER INFORMATION: /replace="Gly"
<220> FEATURE:
<221> NAME/KEY: VARIANT
<222> LOCATION: (19)..(19)
<223> OTHER INFORMATION: /replace="Lys" or "Ala" or "Gly"
<220> FEATURE:
<221> NAME/KEY: VARIANT
<222> LOCATION: (21)..(27)
<223> OTHER INFORMATION: /replace=" "
<220> FEATURE:
<221> NAME/KEY: misc_feature
<222> LOCATION: (21)..(27)
<223> OTHER INFORMATION: /note="This region may or may not be present in
      its entirety"
<220> FEATURE:
<221> NAME/KEY: VARIANT
<222> LOCATION: (29)..(29)
<223> OTHER INFORMATION: /replace="Gln"
<220> FEATURE:
<221> NAME/KEY: VARIANT
<222> LOCATION: (34)..(34)
```

```
<223> OTHER INFORMATION: /replace="Arg" or "Lys" or "any other
      positively charged residue"
<220> FEATURE:
<221> NAME/KEY: VARIANT
<222> LOCATION: (38)..(38)
<223> OTHER INFORMATION: /replace="Phe" or "Lys" or "Arg"
<220> FEATURE:
<221> NAME/KEY: VARIANT
<222> LOCATION: (40)..(40)
<223> OTHER INFORMATION: /replace="homoArg" or "Cit" or "Orn"
<220> FEATURE:
<221> NAME/KEY: VARIANT
<222> LOCATION: (42)..(42)
<223> OTHER INFORMATION: /replace="Nle"
<220> FEATURE:
<221> NAME/KEY: VARIANT
<222> LOCATION: (43)..(43)
<223> OTHER INFORMATION: /replace="Phe" or "Gly" or "Ile"
<220> FEATURE:
<221> NAME/KEY: VARIANT
<222> LOCATION: (46)..(46)
<223> OTHER INFORMATION: /replace="Lys" or "Arg" or "any other
      positively charged residue"
<220> FEATURE:
<221> NAME/KEY: VARIANT
<222> LOCATION: (47)..(47)
<223> OTHER INFORMATION: /replace="Lys" or "Arg" or "any other
      positively charged residue"
<220> FEATURE:
<221> NAME/KEY: VARIANT
<222> LOCATION: (48)..(48)
<223> OTHER INFORMATION: /replace="Lys" or "Arg" or "any other
      positively charged residue"
<220> FEATURE:
<221> NAME/KEY: VARIANT
<222> LOCATION: (49)..(49)
<223> OTHER INFORMATION: /replace="Arg" or "any other positively
      charged residue"
<220> FEATURE:
<221> NAME/KEY: VARIANT
<222> LOCATION: (50)..(50)
<223> OTHER INFORMATION: /replace=" "
<220> FEATURE:
<221> NAME/KEY: VARIANT
<222> LOCATION: (52)..(66)
<223> OTHER INFORMATION: /replace=" "
<220> FEATURE:
<221> NAME/KEY: misc_feature
<222> LOCATION: (52)..(66)
<223> OTHER INFORMATION: /note="This region may or may not be present in
      its entirety"
<220> FEATURE:
<221> NAME/KEY: misc_feature
<222> LOCATION: (1)..(66)
<223> OTHER INFORMATION: /note="Variant residues given in the sequence
      have no preference with respect to those in the annotations
      for variant positions"

<400> SEQUENCE: 4

Ala Arg Glu Asn Glu Met Asp Glu Asn Leu Glu Gln Val Ser Trp Trp
1               5                   10                  15

Trp Ala Asn Leu Arg His Met Ala Leu Asp Met Gly Asn Glu Ile Asp
            20                  25                  30

Thr Gln Asn Arg Gln Ile Asp Arg Ile Met Ala Lys Ala Asp Ser Asn
        35                  40                  45

Lys Thr Arg Ile Asp Glu Ala Asn Gln Arg Ala Thr Lys Met Leu Gly
    50                  55                  60

Ser Gly
65

<210> SEQ ID NO 5
<211> LENGTH: 31
<212> TYPE: PRT
```

<213> ORGANISM: Mus musculus

<400> SEQUENCE: 5

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys Ala Asp
            20                  25                  30

<210> SEQ ID NO 6
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ile Ile Ile Gly Asn Leu Arg His Met Ala Leu Asp Met Gly Asn Glu
1               5                   10                  15

Ile Asp Thr Gln Asn Arg Gln Ile Asp Arg Ile Met Glu Lys Ala Asp
            20                  25                  30

Ser Asn Lys Thr Arg
        35

<210> SEQ ID NO 7
<211> LENGTH: 7
<212> TYPE: PRT
<213> ORGANISM: Mus musculus

<400> SEQUENCE: 7

Arg His Met Ala Leu Asp Met
1               5

<210> SEQ ID NO 8
<211> LENGTH: 14
<212> TYPE: PRT
<213> ORGANISM: Mus musculus

<400> SEQUENCE: 8

Ala Arg Glu Asn Glu Met Asp Glu Asn Leu Glu Gln Val Ser
1               5                   10

<210> SEQ ID NO 9
<211> LENGTH: 15
<212> TYPE: PRT
<213> ORGANISM: Mus musculus

<400> SEQUENCE: 9

Ile Asp Glu Ala Asn Gln Arg Ala Thr Lys Met Leu Gly Ser Gly
1               5                   10                  15

<210> SEQ ID NO 10
<211> LENGTH: 66
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Arg Glu Asn Glu Met Asp Glu Asn Leu Glu Gln Val Ser Gly Ile
1               5                   10                  15

```
Ile Gly Asn Leu Arg His Met Ala Leu Asp Met Gly Asn Glu Ile Asp
             20                  25                  30

Thr Gln Asn Arg Gln Ile Asp Arg Ile Met Glu Lys Ala Asp Ser Asn
         35                  40                  45

Lys Thr Arg Ile Asp Glu Ala Asn Gln Arg Ala Thr Lys Met Leu Gly
     50                  55                  60

Ser Gly
65
```

<210> SEQ ID NO 11
<211> LENGTH: 56
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Glu Gln Val Ser Gly Ile Ile Gly Asn Leu Arg His Met Ala Leu Asp
1               5                  10                  15

Met Gly Asn Glu Ile Asp Thr Gln Asn Arg Gln Ile Asp Arg Ile Met
             20                  25                  30

Glu Lys Ala Asp Ser Asn Lys Thr Arg Ile Asp Glu Ala Asn Gln Arg
         35                  40                  45

Ala Thr Lys Met Leu Gly Ser Gly
     50                  55
```

<210> SEQ ID NO 12
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Ile Ile Gly Asn Leu Arg His Met Ala Leu Asp Met Gly Asn Glu Ile
1               5                  10                  15

Asp Thr Gln Asn Arg Gln Ile Asp Arg Ile Met Glu Lys Ala Asp Ser
             20                  25                  30

Asn Lys Thr Arg Ile Asp Glu Ala Asn Gln Arg Ala Thr Lys Met Leu
         35                  40                  45

Gly Ser Gly
     50
```

<210> SEQ ID NO 13
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Arg His Met Ala Leu Asp Met Gly Asn Glu Ile Asp Thr Gln Asn Arg
1               5                  10                  15

Gln Ile Asp Arg Ile Met Glu Lys Ala Asp Ser Asn Lys Thr Arg Ile
             20                  25                  30

Asp Glu Ala Asn Gln Arg Ala Thr Lys Met Leu Gly Ser Gly
```

<210> SEQ ID NO 14
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

Asp Met Gly Asn Glu Ile Asp Thr Gln Asn Arg Gln Ile Asp Arg Ile
1               5                   10                  15

Met Glu Lys Ala Asp Ser Asn Lys Thr Arg Ile Asp Glu Ala Asn Gln
                20                  25                  30

Arg Ala Thr Lys Met Leu Gly Ser Gly
            35                  40

<210> SEQ ID NO 15
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

Ile Asp Thr Gln Asn Arg Gln Ile Asp Arg Ile Met Glu Lys Ala Asp
1               5                   10                  15

Ser Asn Lys Thr Arg Ile Asp Glu Ala Asn Gln Arg Ala Thr Lys Met
                20                  25                  30

Leu Gly Ser Gly
            35

<210> SEQ ID NO 16
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys Ala Asp Ser
                20                  25                  30

Asn Lys Thr Arg Ile Asp Glu Ala Asn Gln Arg Ala Thr Lys Met Leu
            35                  40                  45

Gly Ser Gly
        50

<210> SEQ ID NO 17
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys Ala Asp Ser
            20                  25                  30

Asn

<210> SEQ ID NO 18
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys Ala
            20                  25                  30

<210> SEQ ID NO 19
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys
            20                  25

<210> SEQ ID NO 20
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu
            20                  25

<210> SEQ ID NO 21
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ile Ile Gly Asn Leu Arg His Met Ala Leu Asp Met Gly Asn Glu Ile
1               5                   10                  15

Asp Thr Gln Asn Arg Gln Ile Asp Arg Ile Met
```

20                  25

<210> SEQ ID NO 22
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gly Asn Leu Arg His Met Ala Leu Asp Met Gly Asn Glu Ile Asp Thr
1               5                   10                  15

Gln Asn Arg Gln Ile Asp Arg Ile Met Glu Lys Ala Asp Ser Asn Lys
            20                  25                  30

Thr

<210> SEQ ID NO 23
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ile Gly Asn Leu Arg His Met Ala Leu Asp Met Gly Asn Glu Ile Asp
1               5                   10                  15

Thr Gln Asn Arg Gln Ile Asp Arg Ile Met Glu Lys Ala Asp Ser Asn
            20                  25                  30

Lys Thr

<210> SEQ ID NO 24
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gly Ile Ile Gly Asn Leu Arg His Met Ala Leu Asp Met Gly Asn Glu
1               5                   10                  15

Ile Asp Thr Gln Asn Arg Gln Ile Asp Arg Ile Met Glu Lys Ala Asp
            20                  25                  30

Ser Asn Lys Thr
        35

<210> SEQ ID NO 25
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ile Ile Ile Gly Asn Leu Arg His Met Ala Leu Asp Met Gly Asn Glu
1               5                   10                  15

Ile Asp Thr Gln Asn Arg Gln Ile Asp Arg Ile Met Glu Lys Ala Asp

```
                    20                  25                  30

Ser Asn Lys Thr
        35

<210> SEQ ID NO 26
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ile Ile Ile Gly Asn Leu Arg His Met Ala Leu Asp Met Gly Asn Glu
1               5                   10                  15

Ile Asp Thr Gln Asn Arg Gln Ile Asp Arg Ile Met Glu Lys Ala Asp
            20                  25                  30

Ser Asn Lys Thr Arg Ile
        35

<210> SEQ ID NO 27
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ile Ile Ile Gly Asn Leu Arg His Met Ala Leu Asp Met Gly Asn Glu
1               5                   10                  15

Ile Asp Thr Gln Asn Arg Gln Ile Asp Arg Ile Met Glu Lys Ala Asp
            20                  25                  30

Ser Asn

<210> SEQ ID NO 28
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ile Ile Ile Gly Asn Leu Arg His Met Ala Leu Asp Met Gly Asn Glu
1               5                   10                  15

Arg Gln Ile Asp Arg Ile Met Glu Lys Ala Asp Ser Asn Lys Thr Arg
            20                  25                  30

<210> SEQ ID NO 29
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Ile Ile Ile Gly Asn Leu Arg His Met Ala Leu Ile Asp Thr Gln Asn
1               5                   10                  15
```

Arg Gln Ile Asp Arg Ile Met Glu Lys Ala Asp Ser Asn Lys Thr Arg
            20                  25                  30

<210> SEQ ID NO 30
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ile Ile Ile Gly Asn Leu Asp Met Gly Asn Glu Ile Asp Thr Gln Asn
1               5                   10                  15

Arg Gln Ile Asp Arg Ile Met Glu Lys Ala Asp Ser Asn Lys Thr Arg
            20                  25                  30

<210> SEQ ID NO 31
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ile Ile Ile Gly Asn Asp Met Gly Asn Glu Ile Asp Thr Gln Asn Arg
1               5                   10                  15

Gln Ile Asp Arg Ile Met Glu Lys Ala Asp Ser Asn Lys Thr Arg
            20                  25                  30

<210> SEQ ID NO 32
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ile Ile Ile Gly Asp Met Gly Asn Glu Ile Asp Thr Gln Asn Arg Gln
1               5                   10                  15

Ile Asp Arg Ile Met Glu Lys Ala Asp Ser Asn Lys Thr Arg
            20                  25                  30

<210> SEQ ID NO 33
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ile Ile Ile Asp Met Gly Asn Glu Ile Asp Thr Gln Asn Arg Gln Ile
1               5                   10                  15

Asp Arg Ile Met Glu Lys Ala Asp Ser Asn Lys Thr Arg
            20                  25

<210> SEQ ID NO 34
<211> LENGTH: 29
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ile Ile Ile Gly Asn Leu Asn Glu Ile Asp Thr Gln Asn Arg Gln Ile
1               5                   10                  15

Asp Arg Ile Met Glu Lys Ala Asp Ser Asn Lys Thr Arg
            20                  25

<210> SEQ ID NO 35
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ile Ile Ile Gly Asn Leu Gly Asn Glu Ile Asp Thr Gln Asn Arg Gln
1               5                   10                  15

Ile Asp Arg Ile Met Glu Lys Ala Asp Ser Asn Lys Thr Arg
                20                  25                  30

<210> SEQ ID NO 36
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ile Ile Ile Gly Asn Leu Met Gly Asn Glu Ile Asp Thr Gln Asn Arg
1               5                   10                  15

Gln Ile Asp Arg Ile Met Glu Lys Ala Asp Ser Asn Lys Thr Arg
                20                  25                  30

<210> SEQ ID NO 37
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ile Ile Ile Gly Asn Leu Leu Asp Met Gly Asn Glu Ile Asp Thr Gln
1               5                   10                  15

Asn Arg Gln Ile Asp Arg Ile Met Glu Lys Ala Asp Ser Asn Lys Thr
                20                  25                  30

Arg

<210> SEQ ID NO 38
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 38

Ile Ile Ile Gly Asn Leu Gly Asn Glu Ile Asp Thr Gln Asn Arg Gln
1               5                   10                  15

Ile Asp Arg Ile Met Glu Lys Ala Asp Ser Asn Lys Arg
            20                  25

<210> SEQ ID NO 39
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ile Ile Ile Gly Asn Leu Gly Asn Glu Ile Asp Thr Gln Asn Arg Gln
1               5                   10                  15

Ile Asp Arg Ile Met Glu Lys Ala Asp Ser Asn Arg
            20                  25

<210> SEQ ID NO 40
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ile Ile Ile Gly Asn Leu Gly Asn Glu Ile Asp Thr Gln Asn Arg Gln
1               5                   10                  15

Ile Asp Arg Ile Met Glu Lys Ala Asp Ser Arg
            20                  25

<210> SEQ ID NO 41
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ile Ile Ile Gly Asn Leu Gly Asn Glu Ile Asp Thr Gln Asn Arg Gln
1               5                   10                  15

Ile Asp Arg Ile Met Glu Lys Ala Lys Ser Asn Lys Arg
            20                  25

<210> SEQ ID NO 42
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ile Ile Ile Ala Lys Leu Gly Asn Glu Ile Asp Thr Arg Asn Arg Gln
1               5                   10                  15

Ile Asp Arg Ile Met Glu Lys Ala Asp Ser Asn Lys Arg
```

20                  25

<210> SEQ ID NO 43
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ile Ile Ile Gly Lys Leu Gly Asn Glu Ile Asp Thr Arg Asn Arg Gln
1               5                   10                  15

Ile Asp Arg Ile Met Glu Lys Ala Asp Ser Asn Lys Arg
                20                  25

<210> SEQ ID NO 44
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ile Ile Ile Ala Lys Leu Gly Gln Glu Ile Asp Thr Arg Asn Arg Gln
1               5                   10                  15

Lys Asp Arg Ile Met Glu Lys Ala Asp Ser Asn Lys Arg
                20                  25

<210> SEQ ID NO 45
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ile Ile Ile Ala Lys Leu Gly Asn Glu Ile Asp Thr Gln Asn Arg Gln
1               5                   10                  15

Lys Asp Arg Ile Met Ala Lys Ala Asp Ser Asn Lys Arg
                20                  25

<210> SEQ ID NO 46
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Ile Ile Ile Ala Lys Leu Gly Asn Glu Ile Asp Thr Arg Asn Arg Gln
1               5                   10                  15

Lys Asp Arg Ile Met Ala Lys Ala Asp Ser Asn Lys Arg
                20                  25

<210> SEQ ID NO 47
<211> LENGTH: 29
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 47

Ile Ile Ile Ala Lys Leu Gly Asn Glu Ile Asp Thr Arg Asn Arg Gln
1               5                   10                  15

Lys Asp Arg Ile Met Glu Lys Ala Lys Ser Lys Lys Arg
            20                  25

<210> SEQ ID NO 48
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (21)..(21)
<223> OTHER INFORMATION: Nle

<400> SEQUENCE: 48

Ile Ile Ile Gly Asn Leu Gly Asn Glu Ile Asp Thr Gln Asn Arg Gln
1               5                   10                  15

Ile Asp Arg Ile Leu Ala Lys Ala Lys Ser Lys Lys Arg
            20                  25

<210> SEQ ID NO 49
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ile Ile Ile Gly Asn Leu Gly Asn Glu Ile Asp Thr Gln Asn Arg Gln
1               5                   10                  15

Ile Asp Arg Ile Met Ala Lys Ala Lys Ser Lys Lys Arg
            20                  25

<210> SEQ ID NO 50
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ile Ile Ile Gly Asn Leu Gly Asn Glu Ile Asp Thr Gln Asn Arg Gln
1               5                   10                  15

Ile Asp Arg Ile Met Glu Lys Ala Arg Arg Lys Lys Arg
            20                  25

<210> SEQ ID NO 51
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 51

Ile Ile Ile Gly Asn Leu Gly Asn Glu Ile Asp Thr Gln Asn Arg Gln
1               5                   10                  15

Ile Asp Arg Ile Met Glu Lys Ala Lys Arg Lys Lys Arg
            20                  25

<210> SEQ ID NO 52
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ile Ile Ile Gly Asn Leu Gly Asn Glu Ile Asp Thr Gln Asn Arg Gln
1               5                   10                  15

Ile Asp Arg Ile Met Glu Lys Ala Lys Lys Lys Lys Arg
            20                  25

<210> SEQ ID NO 53
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Ile Ile Ile Gly Asn Leu Gly Asn Glu Ile Asp Thr Gln Asn Arg Gln
1               5                   10                  15

Ile Asp Arg Ile Met Glu Lys Ala Lys Ser Lys Lys Arg
            20                  25

<210> SEQ ID NO 54
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (19)..(19)
<223> OTHER INFORMATION: homoArg

<400> SEQUENCE: 54

Ile Ile Ile Gly Asn Leu Gly Asn Glu Ile Asp Thr Gln Asn Arg Gln
1               5                   10                  15

Ile Asp Arg Ile Met Ala Lys Ala Lys Ser Lys Lys Arg
            20                  25

<210> SEQ ID NO 55
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (19)..(19)
<223> OTHER INFORMATION: homoArg

<400> SEQUENCE: 55

Ile Ile Ile Gly Asn Leu Gly Asn Glu Ile Asp Thr Gln Asn Arg Gln
1               5                   10                  15

Ile Asp Arg Ile Met Ala Lys Ala Lys Ser Lys Lys Arg
            20                  25

<210> SEQ ID NO 56
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (19)..(19)
<223> OTHER INFORMATION: homoArg

<400> SEQUENCE: 56

Ile Ile Ile Gly Asn Leu Gly Asn Glu Ile Asp Thr Gln Asn Arg Gln
1               5                   10                  15

Ile Asp Arg Ile Met Ala Lys Ala Lys Ser Lys Lys Arg Arg Arg
            20                  25                  30

<210> SEQ ID NO 57
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (19)..(19)
<223> OTHER INFORMATION: homoArg

<400> SEQUENCE: 57

Ile Ile Ile Gly Asn Leu Gly Asn Glu Ile Asp Thr Gln Asn Arg Gln
1               5                   10                  15

Ile Asp Arg Ile Met Ala Lys Ala Lys Ser Lys Lys Arg
            20                  25

<210> SEQ ID NO 58
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (19)..(19)
<223> OTHER INFORMATION: homoArg

<400> SEQUENCE: 58

Trp Trp Trp Gly Asn Leu Gly Asn Glu Ile Asp Thr Gln Asn Arg Gln
1               5                   10                  15

Ile Asp Arg Ile Met Ala Lys Ala Lys Ser Lys Lys Arg
            20                  25

<210> SEQ ID NO 59

```
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (19)..(19)
<223> OTHER INFORMATION: homoArg

<400> SEQUENCE: 59

Trp Trp Trp Ala Lys Leu Gly Gln Glu Ile Asp Thr Arg Asn Arg Gln
1               5                   10                  15

Lys Asp Arg Ile Met Ala Lys Ala Asp Ser Asn Lys Arg
            20                  25

<210> SEQ ID NO 60
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(3)
<223> OTHER INFORMATION: 1-Nal
<220> FEATURE:
<221> NAME/KEY: MOD_RES
<222> LOCATION: (19)..(19)
<223> OTHER INFORMATION: homoArg

<400> SEQUENCE: 60

Ala Ala Ala Ala Lys Leu Gly Gln Glu Ile Asp Thr Arg Asn Arg Gln
1               5                   10                  15

Lys Asp Arg Ile Met Ala Lys Ala Asp Ser Asn Lys Arg
            20                  25

<210> SEQ ID NO 61
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(3)
<223> OTHER INFORMATION: 2-Nal
<220> FEATURE:
<221> NAME/KEY: MOD_RES
<222> LOCATION: (19)..(19)
<223> OTHER INFORMATION: homoArg

<400> SEQUENCE: 61

Ala Ala Ala Ala Lys Leu Gly Gln Glu Ile Asp Thr Arg Asn Arg Gln
1               5                   10                  15

Lys Asp Arg Ile Met Ala Lys Ala Asp Ser Asn Lys Arg
            20                  25

<210> SEQ ID NO 62
<211> LENGTH: 29
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: MOD_RES
<222> LOCATION: (1)..(3)
<223> OTHER INFORMATION: 2-Nal
<220> FEATURE:
<221> NAME/KEY: MOD_RES
<222> LOCATION: (19)..(19)
<223> OTHER INFORMATION: homoArg
<220> FEATURE:
<221> NAME/KEY: MOD_RES
<222> LOCATION: (23)..(23)
<223> OTHER INFORMATION: homoArg

<400> SEQUENCE: 62

Ala Ala Ala Ala Lys Leu Gly Gln Glu Ile Asp Thr Arg Asn Arg Gln
1               5                   10                  15

Lys Asp Arg Ile Met Ala Arg Ala Asp Ser Asn Lys Arg
            20                  25

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ile Ile Ile Gly Asn Leu
1               5

<210> SEQ ID NO 64
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Phe Phe Phe Phe
1

<210> SEQ ID NO 65
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Phe Phe Phe Gly Asn Leu
1               5

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66
```

Phe Phe Phe Phe Phe Gly Asn Leu
1               5

<210> SEQ ID NO 67
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Trp Trp Gly Asn Leu
1               5

<210> SEQ ID NO 68
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Trp Trp Trp Gly Asn Leu
1               5

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(2)
<223> OTHER INFORMATION: 1-Nal

<400> SEQUENCE: 69

Ala Ala Gly Asn Leu
1               5

<210> SEQ ID NO 70
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(3)
<223> OTHER INFORMATION: 1-Nal

<400> SEQUENCE: 70

Ala Ala Ala Gly Asn Leu
1               5

<210> SEQ ID NO 71
<211> LENGTH: 7
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"
<220> FEATURE:
<221> NAME/KEY: MOD_RES
<222> LOCATION: (1)..(4)
<223> OTHER INFORMATION: 1-Nal

<400> SEQUENCE: 71

Ala Ala Ala Ala Gly Asn Leu
1               5
```

PEPTIDE SUBSTRATES RECOGNIZABLE BY TYPE E BOTULINUM NEUROTOXIN

GOVERNMENT FUNDING

Research supporting this application was carried out by the United States of America as represented by the Secretary, Department of Health and Human Services.

CROSS REFERENCE TO RELATED APPLICATIONS

This application is a National Stage of International Patent Application PCT/US2013/073885, filed 9 Dec. 2013, which is incorporated herein by reference in its entirety.

INCORPORATION BY REFERENCE

In compliance with 37 C.F.R. § 1.52(e)(5), the sequence information contained in electronic file name: 1420378_419US9_Sequence_Listing_ST25.txt; size 39.5 KB; created on: 23 May 2017; using Patent-In 3.5, and Checker 4.4.0 is hereby incorporated herein by reference in its entirety.

BACKGROUND OF THE INVENTION

The neurotoxins produced by *Clostridium botulinum* (Botulinum Neurotoxins, BoNT) are among the most poisonous substances known. The neurotoxin type E (BoNT/E) forms part of a family of seven related serotypes (botulinum toxins A to G) produced by different strains of *Clostridium botulinum*. The major types of human diseases caused by these toxins include food-borne botulism, infant botulism, wound botulism, and adult interstinal colonization. But these toxins can also constitute a potential biological weapon to the extent that they are easy to produce. On the other hand, for several years, the botulinum toxins, have been used for therapeutic (dystonia, neuronal hyperactivity such as strabismus, blepharospasm etc.) or aesthetic applications (in particular wrinkle reduction). For all these applications, it is essential to have a simple, quick and sensitive method for the detection and quantification of botulinum toxin in various media, including biological media.

The botulinum neurotoxins are synthesized by *C. botulinum* as inactive single chain polypeptides of 150 kDa which undergo proteolytic cleavage to generate active holotoxins constituting of two protein sub-units: a heavy chain (100 kD) linked to a light chain (50 kD) via a disulfide bridge. The heavy chain is involved in the binding of the toxin to the nerve ending, in the internalization then in the translocation of the light chain into the cytosol. The light chain is responsible for the toxicity of the protein by inhibition of the calcium-dependent release of acetylcholine. Unlike some types of botulinum neurotoxins (e.g. type A) that are generated as active dichain form, BoNT/E is released from the bacterium in an inactive form that must be activated by exposing to exogenous proteases such as trypsin.

The toxicity of the light chain of these toxins is due to its peptidase activity. In fact, the botulinum toxins belong to the family of zinc metallopeptidases and more particularly to the sub-family of the zincins which contain the consensus sequence HExxH; (Schiavo et al. (1992) J. Biol. Chem. 267, 23479-23483; Roques B. P. (1993) Biochem. Soc. Trans. 21, 678-685). They cleave very specifically the neuronal proteins involved in the exocytosis of the neurotransmitters, such as SNAP-25 and synaptobrevin. The cleavage site is specific to each toxin, including to an identical substrate. Botulinum toxin type E cleaves specifically one of the SNARE complex proteins, SNAP-25 (Chen et al., J Biol Chem. 2006 Apr. 21; 281(16): 10906-11, incorporated by reference in its entirety herein).

There are several challenges in the diagnosis and treatment of botulism. Since the toxicity of BoNT is so great, it is necessary to detect BoNT at very low concentrations, preferably as the active toxin. It is also imperative that the diagnosis be made rapidly since the equine-based treatment can have several substantial side effects.

The current standard for detecting botulinum toxins in a sample is the determination of the median lethal dose (LD50) in mice (Kautter and Salomon (1976) J. Assoc. Anal. Chem., 60, 541-545; incorporated by reference in its entirety herein). The mouse bioassay is currently the gold standard and is the only widely accepted method for the detection of BoNT. Mixtures of neutralizing antibodies are given to mice in conjunction with the sample in question to differentiate the toxin serotype. Mice receiving the appropriate anti-BoNT serotype antibody along with the toxic sample do not show symptoms and survive, while mice treated with the other serotype antibodies show symptoms and die. Importantly, this assay measures only active toxin. The mouse bioassay is very sensitive, detecting as little as 10 picograms (pg) of active toxin which is defined as 1 mouse $LD_{50}$ ($mLD_{50}$) or 1 unit of BoNT. However, the mouse bioassay can be slow (taking up to 4 days) for final results and it requires the sacrifice of many animals. It is highly desirable to have a more rapid technique of detecting botulinum toxins.

The ELISA is much more rapid, but is less sensitive, is problematic in certain matrices, shows cross reactivity between BoNT serotypes, and measures inactive toxin along with active toxin. The ELISA is currently used primarily as a fast screening technique and results are verified by the mouse bioassay.

Accordingly, it is an object of the present invention to provide such a sensitive detection and differentiation method for detecting botulinum neurotoxins using novel peptide substrates.

SUMMARY OF THE INVENTION

The present invention is based, at least in part, on the discovery of novel peptide substrates selectively recognized by type E botulinum neurotoxin (BoNT/E), and their uses, in particular for carrying out methods for detecting, identifying and/or dosing botulinum toxin type E.

Accordingly, in a first aspect, the present invention features a peptide substrate selectively recognized by BoNT/E comprising the sequence:

(SEQ ID NO: 3)
$X_1X_2X_3X_4X_5LX_6GX_7EIDTX_8NRQX_9DX_{10}IX_{11}X_{12}KAX_{13}X_{14}X_{15}$
$X_{16}X_{17}$, wherein:
$X_1$, $X_2$ or $X_3$: W, 1-Nal (1-Naphthylalanine), 2-Nal, F, Y, I, L, Nle (norleucine), A, or any other hydrophobic amino acid residue;
$X_4$: A or G;
$X_5$: N, K, A, or G;
$X_6$: No residue, or RHMALDM;
$X_7$: N or Q;
$X_8$: Q, R, K or any other positively charged residue;

$X_9$: I, F, K, or R;
$X_{10}$: R, homoArg, Cit (citrulline) or Orn (ornithine);
$X_{11}$: M or Nle;
$X_{12}$: A, F, G, I;
$X_{13}$: D, K, R or any other positively charged residue;
$X_{14}$: S, K, R or any other positively charged residue;
$X_{15}$: N, K, R or any other positively charged residue;
$X_{16}$: K, R or any other positively charged residue; and
$X_{17}$: R, TR; native or amidated C-terminus.

In one embodiment, RHMALDM (SEQ ID NO: 7) corresponds to residues 161-167 of SNAP-25 (SEQ ID NO:1).

In another aspect, the present invention features a peptide substrate selectively recognized by BoNT/E comprising the sequence $(X_0)_m$-(SEQ ID NO:3)-$(X_{18})_n$(SEQ ID NO:4), wherein,
m: 0 or 1;
n: 0 or 1;
$X_0$: ARENEMDENLEQVS; and
$X_{18}$: IDEANQRATKMLGSG.

In one embodiment, ARENEMDENLEQVS (SEQ ID NO: 8) corresponds to residues 141-154 of SEQ ID NO:1.

In another embodiment, IDEANQRATKMLGSG (SEQ ID NO: 9) corresponds to residues 192-206 of SEQ ID NO:1.

In another aspect, the present invention features a peptide substrate selectively recognized by BoNT/E comprising IIGNLRHMALDMGNEIDTQNRQIDRIMEKADSNKT (SEQ ID NO:2), wherein SEQ ID NO:2 comprises one or more of the following alterations:
  truncation of the N- or C-terminal sequence;
  extension of the N- or C-terminal sequence;
  one or more deletions; and
  one or more mutations.

In one embodiment, the extension comprises the addition one or more amino acids selected from the group consisting of isoleucine (Ile) and arginine (Arg).

In another embodiment, the deletion comprises the deletion of seven internal residues (RHMALDM).

In another further embodiment, the deletion comprises the deletion of three N-terminal residues NTK.

In one embodiment of any one of the above aspect, the peptide substrate further comprises a FRET pair. In one embodiment, the FRET pair is on the C or N-termini. In another embodiment, the FRET pair is contained within the sequence.

In preferred embodiments of any one of the aspects herein, the peptide substrate is a synthetic peptide substrate.

In another aspect, the present invention features a method for detecting the presence of clostridial botulinum neurotoxin serotype E (BoNT/E) in a sample comprising the steps of a) mixing a sample that may comprise serotype E of clostridial neurotoxins with magnetic beads where specific antibodies against BoNT/E are immobilized to capture toxins; b) washing toxin-captured beads; c) transferring toxin-captured beads into a reaction solution that contains a peptide substrate selectively recognized by BoNT/E, such that at least a portion of the amount of the substrate is proteolytically cleaved to produce a mixture comprising uncleaved substrate and peptide cleavage products; d) analyzing the mixture on a mass spectrometer to produce a signal corresponding to the mass of at least one peptide cleavage product; e) using the signal corresponding to the peptide cleavage products to identify the presence of clostridial neurotoxin serotype E; and f) quantitating the amount of proteolytic cleavage of the peptide substrate for the clostridial neurotoxin serotype by mass spectrometry using a stable isotope labeled internal standard that has identical sequence to a cleavage product, wherein the amount of active toxin of BoNT/E in the sample is about 0.05-0.1 pg or more.

In still another aspect, the present invention features a method for diagnosing infection by clostridial botulinum neurotoxin serotype E (BoNT/E) in a sample comprising the steps of a) mixing a sample that may comprise serotype E of clostridial neurotoxins with a peptide substrate selectively recognized by BoNT/E, such that at least a portion of the amount of the substrate is proteolytically cleaved to produce a mixture comprising uncleaved substrate and peptide cleavage products; b) analyzing the mixture on a mass spectrometer to produce a signal corresponding to the mass of at least one peptide cleavage product; c) using the signal corresponding to the peptide cleavage products to identify the presence of clostridial neurotoxin serotype E; and d) quantitating the amount of proteolytic cleavage of the peptide substrate for the clostridial neurotoxin serotype by mass spectrometry, wherein the amount of active toxin of BoNT/E in the sample is about 0.1 pg or more.

In one embodiment, the peptide substrate comprises any one of the peptide substrates of any one of the above aspects or embodiments.

In a further embodiment, the mass spectrometry is selected from matrix-assisted laser desorption-ionization time of flight mass spectrometry (MALDI-TOF-MS) and high performance liquid chromatography-electrospray ionization-tandem mass spectrometry (LC-ESI-MS/MS).

In another embodiment, the method further comprises a control sample. In a further embodiment, the control sample is a defined negative BoNT/E sample or a defined positive BoNT/E sample.

In another aspect, the invention features a kit, comprising any one of the peptide substrates of any one of the peptide substrates of any one of the above aspects or embodiments, and BoNT/E.

Other aspects of the invention are described in, or are obvious from, the following disclosure, and are within the ambit of the invention.

BRIEF DESCRIPTION OF THE DRAWINGS

FIG. 2 is a table (Table 4) that shows the effect of single amino acid mutations on the detection of cleavage product of mutated peptide-32 by BoNT/E. X represents norleucine.

FIG. 4 shows detection of various amount of BoNT/E spiked in 0.5 mL of serum or stool matrices.

FIG. 5 shows detection of the cleavage product of the Peptide#62 cleaved by BoNT/E complex spiked in stool matrix (0.5 mL) at a broad range of toxin concentrations.

DETAILED DESCRIPTION OF THE INVENTION

Figure 1:
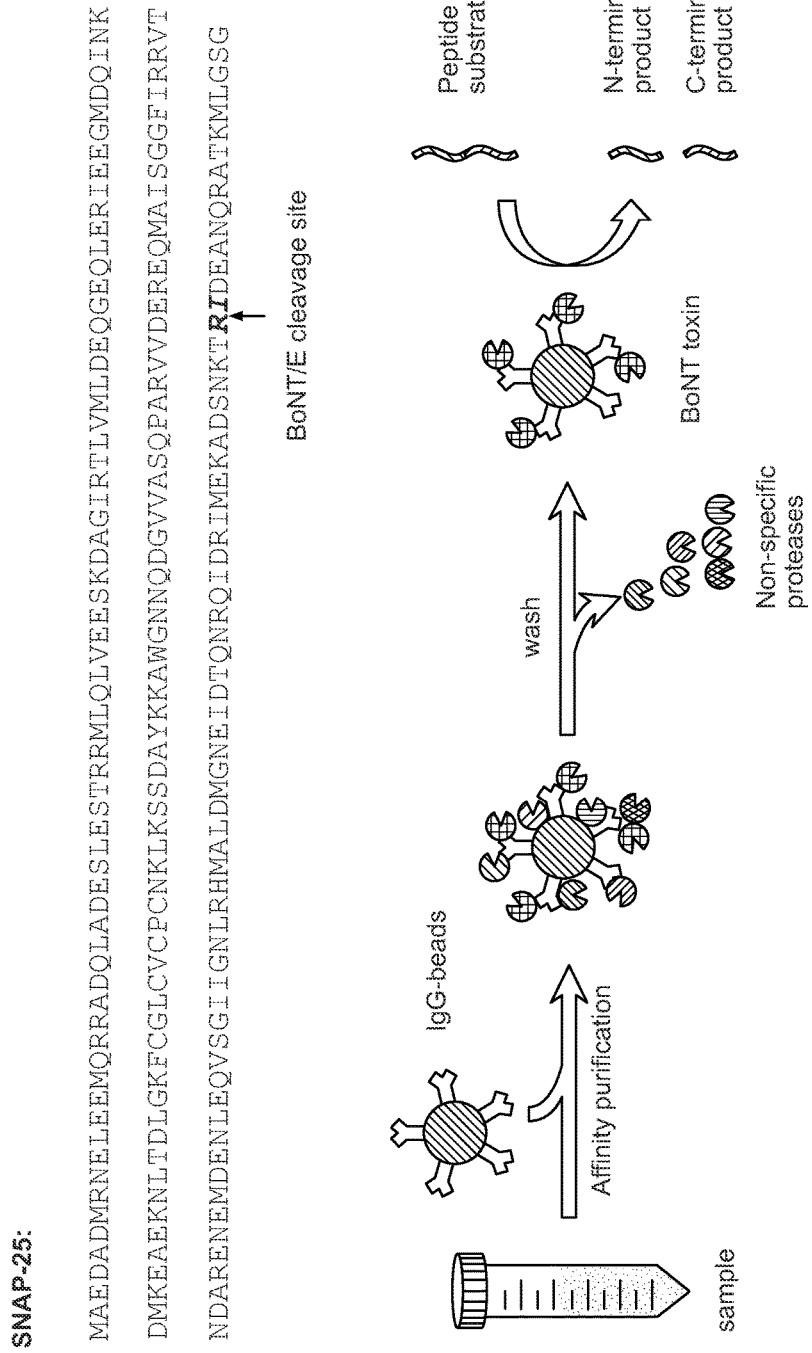
FIG. 1 shows the sequence of the native protein substrate of BoNT/E, SNAP-25 (top; SEQ ID NO: 1) and the scheme of Endopep-MS assay for the detection of BoNTs using a peptide substrate (bottom).
Figure 3:
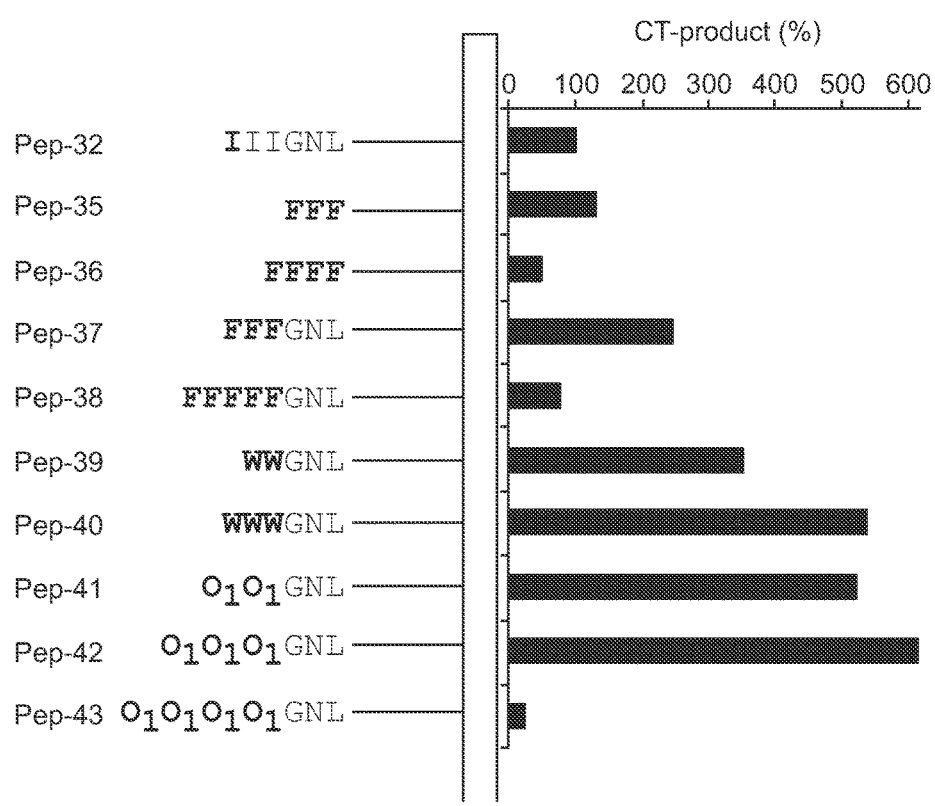
FIG. 3 shows cleavage of the peptides with N-terminal hydrophobic residues. $O_1$: 1-Nal

The present invention relates to peptide substrates selectively recognized by botulinum toxin type E, BoNT/E, and their uses, in particular for carrying out methods for detecting, identifying and/or dosing botulinum toxin type E.
Definitions
The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

As used herein, "botulinum toxin serotype E" is synonymous with "BoNT/E," "type E," or similar terminology referring unambiguously to *Clostridium botulinum* neurotoxin type E. BoNT/E is meant to refer to any of a number of polypeptide neurotoxins, and derivatives thereof, which can be purified from *Clostridium botulinum* serotype E strains. Exemplary strains of BoNT/E include, but are not limited to, the following, referenced by NCBI Accession number:

| BoNT/E subtypes | Accession Number |
|---|---|
| E1 | JX424539 |
| E2 | JX424535 |
| E3 | GQ294552 |
| E4 | X62088 |
| E5 | AB037711 |
| E6 | AM695765 |
| E7 | JX424537 |
| E8 | JN695730 |
| E9 | JX424534 |

As used herein, a "composition" refers to an active agent (e.g., peptides of the invention). The composition additionally can comprise a pharmaceutically acceptable carrier or excipient and/or one or more therapeutic agents for use in vitro or in vivo.

As used herein, a "control sample" means a defined negative BoNT/E sample or a defined positive BoNT/E sample. As used herein, the term "sample" means any biological matter that contains or potentially contains an active BoNT/E.

As used herein, the term "Fluorescence Resonance Energy Transfer (FRET) pair" is meant to refer to a donor and acceptor molecule that are in close proximity to one another (typically 10-100 Å). The absorption or excitation spectrum of the acceptor must overlap the fluorescence emission spectrum of the donor.

As used herein, "kits" are understood to contain at least the non-standard laboratory reagents of the invention and one or more non-standard laboratory reagents for use in the methods of the invention.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

As used herein, the term "synthetic peptide" is meant to refer to any peptide generate by chemical synthesis.

As used herein, the term "subject" is intended to include organism needing detection or treatment. Examples of subjects include mammals, e.g., humans, dogs, cows, horses, pigs, sheep, goats, cats, mice, rabbits, rats, and transgenic non-human animals. In certain embodiments, the subject is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

Any compositions or methods provided herein can be combined with one or more of any of the other compositions and methods provided herein.

Other definitions appear in context throughout the disclosure.

Compositions

Described herein are peptide substrates, including synthetic peptide substrates, that can be used for the specific detection of BoNT/E. The native peptide substrate of BoNT/E is synaptosomal-associated protein 25 (SNAP-25). SNAP-25 is a t-SNARE protein that is encoded by the SNAP25 gene in humans. SNAP-25 is a component of the trans-SNARE complex. SNAP25 corresponds to RefSeq (mRNA) NM_003081 (human) and NM_011428 (mouse) and RefSeq (protein) NP_003072 (human) and NP_035558 (mouse).

The sequence of SNAP-25 is represented by SEQ ID NO: 1, shown below. The BoNT/E cleavage site is highlighted in bold and underlined.

```
                                            SEQ ID NO: 1
 1          11          21          31
MAEDADMRNE  LEEMQRRADQ  LADESLESTR  RMLQLVEESK 41          51          61          71
DAGIRTLVML  DEQGEQLERI  EEGMDQINKD  MKEAEKNLTD 81          91          101         111
LGKFCGLCVC  PCNKLKSSDA  YKKAWGNNQD  GVVASQPARV 121         131         141         151
VDEREQMAIS  GGFIRRVTND  ARENEMDENL  EQVSGIIGNL 161         171         181         191
RHMALDMGNE  IDTQNRQIDR IMEKADSNKT  RIDEANQRAT

201
KMLGSG
```

The novel compositions of the present invention optimize the current peptide substrate (SEQ ID NO:2) for the detection of BoNT/E. SEQ ID NO:2 corresponds to SNAP-25 positions 156-190 (S. R. Kalb et al. International Journal of Mass Spectrometry (2008), 278, 101-108; b) S. R. Kalb et al. The Botulinum J. (2012), 2(2), 119-134). The BoNT/E cleavage site is highlighted in bold.

```
                                       SEQ ID NO: 2
IIGNLRHMALDMGNEIDTQNRQIDRIMEKADSNKT
```

Accordingly, the present invention features peptide substrates that are selectively recognized by BoNT/E. In exemplary embodiments, the peptide substrate is represented by SEQ ID NO:3, shown below. The bold and underlined residues are the cleavage site of BoNT/E substrates.

```
                                                    SEQ ID NO: 3
X1X2X3X4X5LX6GX7EIDTX8NRQX9DX10IX11X12KAX13X14X15
X16X17,
``` wherein:

$X_1$, $X_2$ or $X_3$: W, 1-Nal (1-Naphthylalanine), 2-Nal, F, Y, I, L, Nle (norleucine), A, or any other hydrophobic residue;

$X_4$: A or G;

$X_5$: N, K, A, or G;

$X_6$: No residue, or RHMALDM;

$X_7$: N or Q;

$X_8$: Q, R, K or any other positively charged residue;

$X_9$: I, F, K, or R;

$X_{10}$: R, homoArg, Cit (citrulline) or Orn (ornithine);

$X_{11}$: M or Nle;

$X_{12}$: A, F, G, I;

$X_{13}$: D, K, R or any other positively charged residue;

$X_{14}$: S, K, R or any other positively charged residue;

$X_{15}$: N, K, R or any other positively charged residue;

$X_{16}$: K, R or any other positively charged residue; and $X_{17}$: R, TR; native or amidated C-terminus.

RHMALDM corresponds to residues 161-167 of SEQ ID NO:1 (SNAP-25).

In other exemplary embodiments, the peptide substrate is represented by SEQ ID NO: 4, shown below.

```
                                                    SEQ ID NO: 4
(X0)m-(SEQ ID NO: 3)-(X18)n,
``` wherein, m: 0 or 1;

n: 0 or 1;

$X_0$: ARENEMDENLEQVS; and $X_{18}$: IDEANQRATKMLGSG.

ARENEMDENLEQVS corresponds to residues 141-154 of SEQ ID NO:1.

IDEANQRATKMLGSG corresponds to residues 192-206 of SEQ ID NO:1.

SEQ ID NO:4 is derived based on extensive experiments that show cleavage efficiency of peptides with the native sequence of SNAP-25 (141-206), SNAP-25 (156-206), SNAP-25 (156-190) (see examples section below).

The present invention also contemplates any of the peptides described herein with any FRET pair on the termini or within the sequences of SEQ ID NO:3 and SEQ ID NO: 4. For example, one common pair fluorophores for biological use is a cyan fluorescent protein (CFP)—yellow fluorescent protein (YFP) pair. In the absence of BoNT/E, the reporter is intact and the CFP and YFP moieties are in close proximity. Excitation of CFP results in energy transfer to YFP due to FRET. As a consequence, CFP emission is quenched while YFP emits fluorescence due to FRET. In the presence of BoNT, the reporter is cleaved by the proteolytic activity of BoNT/E. The CFP and YFP moieties are physically separated and FRET can no longer occur. CFP emission is restored and YFP emission is reduced. Adding FRET tags into the novel peptides disclosed herein should generate higher detection than the FRET substrates that are commercially available (e.g. BOTEST A/E or SNAP ETIDE).

The peptide substrates of the present invention advantageously have a low limit of detection of BoNT/E, as low as 0.05-0.1 mouse $LD_{50}$/ml.

In another non-limiting embodiment, the present invention features a peptide substrate selectively recognized by BoNT/E comprising IIGNLRHMALDMGNEIDTQNRQIDRIMEKADSNKT (SEQ ID NO:2), wherein SEQ ID NO:2 comprises one or more alterations. The one or more alterations can be truncation of the N- or C-terminal sequence; extension of the N- or C-terminal sequence; one or more deletions; and one or more mutations.

In one embodiment, the peptides of the invention comprise a truncation of the N-terminal sequence. In another embodiment, the peptides of the invention comprise a truncation of the C-terminal sequence. By truncation is meant a deletion in one or more amino acids of the N- or C-terminal sequence, for example 1, 2, 3, 4, 5, 6, 7, 8, 9, 10 or more.

In one embodiment, the peptides of the invention comprise an extension of the N-terminal sequence. In another embodiment, the peptides of the invention comprise an extension of the C-terminal sequence. By extension is meant an addition of one or more amino acids in the N- or C-terminal sequence, for example 1, 2, 3, 4, 5, 6, 7, 8, 9, 10 or more. In exemplary embodiment, the extension comprises the addition one or more amino acids selected from the group consisting of: isoleucine (Ile) and arginine (Arg).

In another embodiment, the peptides of the invention comprise one or more deletions. In an exemplary embodiment, the deletion comprises the deletion of seven internal residues (RHMALDM). In another exemplary embodiment, the deletion comprises the deletion of three N-terminal residues (NTK).

Preferably, the peptides of the invention are synthetic peptides generated by chemical synthesis.

In another further embodiment, the peptides of the invention comprise one or more mutations. A mutation can be, e.g. a substitution, a deletion or an addition.

Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

To determine the percent identity of two amino acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLASTN and BLASTX programs of Altschul, et al. (1990) J. Mol. Biol. 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) Nucleic Acids Res. 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. Another preferred, non-limiting example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448. When using the FASTA algorithm for comparing nucleotide or amino acid sequences, a PAM120 weight residue table can, for example, be used with a k-tuple value of 2.

The present invention also pertains to variants of the peptide substrates selectively recognized by BoNT/E. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a peptide substrate selectively recognized by BoNT/E which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the marker proteins from a degenerate oligonucleotide sequence. Methods for synthesizing degenerate oligonucleotides are known in the art (see, e.g., Narang, 1983, Tetrahedron 39:3; Itakura et al., 1984, Annu. Rev. Biochem. 53:323; Itakura et al., 1984, Science 198:1056; Ike et al., 1983 Nucleic Acid Res. 11:477).

In addition, libraries of segments of a peptide substrate selectively recognized by BoNT/E can be used to generate a variegated population of polypeptides for screening and subsequent selection of variant marker proteins or segments thereof. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S 1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a peptide substrate selectively recognized by BoNT/E of the invention (Arkin and Yourvan, 1992, Proc. Natl. Acad. Sci. USA 89:7811-7815; Delgrave et al., 1993, Protein Engineering 6(3):327-331).

Methods

A method for the detection and differentiation of BoNTs has been described in U.S. Pat. No. 7,611,856 (incorporated by reference in its entirety herein), which utilizes the high specificity of the enzymatic toxin with the high specificity of mass spectroscopy (MS). This MS-based method allows the detection of enzymatic activity of all the BoNT serotypes. The present invention is based, at least in part, on the discovery of novel peptide substrates selectively recognized by type E botulinum neurotoxin (BoNT/E), and their uses, in particular for carrying out methods for detecting, identifying and/or dosing botulinum toxin type E. The peptide substrates of the present invention provide a considerable improvement when compared to the established substrate for BoNT/E detection.

Accordingly, the methods of the invention encompass methods for detecting the presence of clostridial botulinum neurotoxin serotype E (BoNT/E) in a sample and methods of diagnosing infection by clostridial botulinum neurotoxin serotype E (BoNT/E) in a sample.

A sample is meant to refer to any biological matter that contains or potentially contains an active BoNT/E. Exemplary samples include bacterial, baculoviral and yeast lysates; raw, cooked, partially cooked or processed foods; beverages; animal feed; soil samples; water samples; pond sediments; lotions; cosmetics; and clinical formulations. It is understood that the term sample encompasses tissue samples, including, without limitation, mammalian tissue samples; livestock tissue samples such as sheep, cow and pig tissue samples; primate tissue samples; and human tissue samples. Such samples encompass, without limitation, intestinal samples such as infant intestinal samples, tissue samples obtained from a wound. In certain embodiments, the sample is from a human subject. In further embodiments, the human subject is an infant. Other such samples include mammalian tissue, mammalian saliva, mammalian excretions and mammalian feces. For example, as a non-limiting example, a method of the invention can be useful for detecting the presence or activity of a BoNT/E in a food or beverage sample; to assay a sample from a human or animal, for example, exposed to a BoNT/E or having one or more symptoms of a BoNT/E exposure; to follow activity during production and purification of BoNT/E; or to assay formulated BoNT/E products such as pharmaceuticals or cosmetics.

In certain embodiments, the sample is selected from the group consisting of milk, yogurt, cheese, beef, sausage, serum, and stool.

There is no limit to the size of the sample. In certain cases, there may be a need to perform the claimed methods with clinical samples in larger volumes (100 µL to 1 mL).

In other non-limiting examples, methods for detecting the presence of clostridial botulinum neurotoxin serotype E (BoNT/E) in a sample comprise the steps of a) mixing a sample that may comprise serotype E of clostridial neurotoxins with magnetic beads where specific antibodies against BoNT/E are immobinized to capture toxins; b) washing toxin-captured beads; c) transferring toxin-captured beads into a reaction solution that contains a peptide substrate selectively recognized by BoNT/E, such that at least a portion of the amount of the substrate is proteolytically cleaved to produce a mixture comprising uncleaved substrate and peptide cleavage products; d) analyzing the mixture on a mass spectrometer to produce a signal corresponding to the mass of at least one peptide cleavage product; e) using the signal corresponding to the peptide cleavage products to identify the presence of clostridial neurotoxin serotype E; and f) quantitating the amount of proteolytic cleavage of the peptide substrate for the clostridial neurotoxin serotype by mass spectrometry using a stable isotope labeled internal standard that has identical sequence to a cleavage product, wherein the amount of active toxin of BoNT/E in the sample is about 0.05-0.1 pg or more. In certain embodiments, the amount of active toxin of BoNT/E in the sample is about 0.05, 0.06, 0.07, 0.08, 0.09, 0.1, 0.11, 0.12, 0.13, 0.14, 0.15, 0.16, 0.17, 0.18, 0.19 pg or more.

The invention also features in other non-limiting examples methods for diagnosing infection by clostridial botulinum neurotoxin serotype E (BoNT/E) in a sample comprising the steps of a) mixing a sample that may comprise serotype E of clostridial neurotoxins with a peptide substrate selectively recognized by BoNT/E, such that at least a portion of the amount of the substrate is proteolytically cleaved to produce a mixture comprising uncleaved substrate and peptide cleavage products; b) analyzing the mixture on a mass spectrometer to produce a signal corresponding to the mass of at least one peptide cleavage product; c) using the signal corresponding to the peptide cleavage products to identify the presence of clostridial neurotoxin serotype E; and d) quantitating the amount of proteolytic cleavage of the peptide substrate for the clostridial neurotoxin serotype by mass spectrometry, wherein the amount of active toxin of BoNT/E in the sample is about 0.05-0.1 pg or more. In certain embodiments, the amount of active toxin of BoNT/E in the sample is about 0.05, 0.06, 0.07, 0.08, 0.09, 0.1, 0.11, 0.12, 0.13, 0.14, 0.15, 0.16, 0.17, 0.18, 0.19 pg or more.

Suitable mass spectrometry techniques can include matrix-assisted laser desorption-ionization time of flight mass spectrometry (MALDI-TOF-MS) and high performance liquid chromatography-electrospray ionization-tandem mass spectrometry (LC-ESI-MS/MS). Other mass spectroscopy techniques may also be employed for analysis of the BoNT/E product peptides. MS-based techniques such as MALDI-TOF-MS can allow screening of hundreds of samples per hour for BoNT/E enzymatic activity. While LC-ESI-MS/MS is much slower than MALDI-TOF-MS, it still offers high specificity and sensitivity and allows accurate quantitative measurements of the levels of BoNT. The MALDI-TOF-MS screening method has been used to detect specific fragments of peptides cleaved by BoNT/E in a pure reaction buffer or within various environmental and clinical type matrices such as milk, sausage, serum and stool spiked with BoNT/E complex. The MALDI-TOF-MS and LC-ESI-MS/MS screening methods can be used to detect specific fragments of peptides cleaved by E in a pure reaction buffer or within various environmental and clinical type matrices, as described herein.

In the methods of the present invention, a target sample can be mixed with the peptide serving as a substrate for proteolytic activity of a botulinum neurotoxin, in particular BoNT/E. After a digestion period of from a few minutes to a few hours, preferably from about 30 minutes to about 2 hours, the product peptides (both an N-terminated fragment and a C-terminated fragment) can be recovered from any matrix using affinity tags on the substrate peptide and therefore unequivocally identified and quantified by mass spectroscopy.

The methods of the present invention are fast, sensitive and specific and can be used as a high-throughput assay for the detection and quantification of BoNT/E activity in a variety of sample types.

Affinity tags such as biotin may be attached on both sides of the cleavage site on the substrate such that after cleavage the products from the cleavage can be collected and separated from any matrix and sample contaminants, as well as, from the toxins. The recovery of both unreacted substrate and cleavage products can be used for calibration and control experiment purposes.

The mass spectroscopy approach to analysis of the products allows a quantification of the amount of neurotoxin since the ratio of the products to the internal standard can be determined, the length of time of digestion will be known and the amount of internal standard will be known so that a calibration curve may be calculated and allow the quantification of the amount of neurotoxin.

The methods of the present invention are useful for detecting small amounts of BoNT/E in a rapid, animal-free assay. The methods of the present invention are contemplated to be performed with reaction volumes from 10-20 µL, preferably 20 µL for example, consisting of BoNTE, reaction buffer, and peptide substrate, with detection of the cleavage of the peptide substrate through mass spectrometry. However, there may be a need to perform this assay with clinical samples in larger volumes (100 µL to 1 mL) and such an additional step may be preferred in those instances. When working with clinical or food samples, there are abundant proteases which cleave either the peptide substrate or other proteases, producing a large number of uninteresting peptides. Therefore, it becomes necessary to pursue a method to capture and concentrate BoNT from a larger volume (100 µL to 1 mL) of a clinical or other type of sample. Because mass spectrometers detect peptides based on their ionization efficiencies, it is critical to analyze a sample which preferentially contains an enriched sample of the peptides of interest in order for those peptides to ionize at their optimum level. Therefore, an affinity method of selecting for the peptides generated from the cleavage of the peptide substrate by BoNT/E may be used for ultimate detection in complex biological samples. Biotinylated peptides may be used in conjunction with avidin affinity chromatography to purify the peptides prior to the mass spectrometric analysis. It should be noted that other tagging platforms could be used here as well such as, e.g., fluorescent tagged peptides (see, e.g., U.S. Pat. No. 6,803,475); however, the avidin-biotin bond is one of the strongest bonds in biology.

The methods of the invention are highly sensitive. For BoNT/E, as little as 0.05-0.1 mouse $LD_{50}$/ml of BoNT/E in a sample can yield sufficient quantities of product peptides to be clearly detected by MALDI-TOF-MS. This is 100 times lower than can be detected by the mouse bioassay. Additionally, this small amount of toxin can be detected and the toxin type differentiated in a single measurement.

The quantification of the amount of active BoNT/E in a sample is important. MALDI-TOF-MS is very rapid and is appropriate for relative quantification, but has limited capability for absolute quantification since the spectra tend to show larger variations than other mass spectral techniques. Thus, a LC-ESI/MS/MS technique that can quantitatively detect BoNT/E activities has been developed. This method is highly specific, since correct identification of the BoNT product peptides depends on both a retention time match with respect to standards, and on a chemical-specific fragmentation (a precursor to product ion multiple reaction monitoring (MRM) transition) monitored by tandem MS. To further enhance specificity, two separate MRM transitions are monitored for each peptide. In addition, the LC-ESI/MS/MS technique can be very sensitive, because it uses a triple quadrupole-based instrument. Absolute quantification of the BoNT/E product peptides is achieved using a stable isotope labeled cleavage product peptide (any other stable peptide which is neither a substrate nor an cleavage product may be used) as an internal standard to correct for any instrumental variations. Typical LC-ESI/MS/MS chromatograms were obtained during the quantification of the activity of BoNT E along with a standard curve for one of the product peptides. Based on obtained data, it is estimated that it should be possible to achieve absolute quantification to within less than 10-20% of the true BoNT/E activity level. Identical LC-ESI/MS/MS strategies can be used to quantify each of the BoNT serotypes. The amount of product peptides produced in a BoNT/E reaction may be correlated to the amount of active toxin in the sample.

The following examples are put forth so as to provide those of ordinary skill in the art with a complete disclosure and description of how to make and use the present invention, and are not intended to limit the scope of what the inventors regard as their invention.

EXAMPLES

The SEQ ID NOS for each of the peptides of the examples are as follows:
  SEQ ID NO: 10 is Pep-1
  SEQ ID NO: 11 is Pep-2
  SEQ ID NO: 12 is Pep-3
  SEQ ID NO: 13 is Pep-4
  SEQ ID NO: 14 is Pep-5
  SEQ ID NO: 15 is Pep-6
  SEQ ID NO: 16 is Pep-7
  SEQ ID NO: 2 is Pep-8
  SEQ ID NO: 17 is Pep-9
  SEQ ID NO: 5 is Pep-10
  SEQ ID NO: 18 is Pep-11
  SEQ ID NO: 19 is Pep-12
  SEQ ID NO: 20 is Pep-13
  SEQ ID NO: 21 is Pep-14
  SEQ ID NO: 22 is Pep-15
  SEQ ID NO: 23 is Pep-16
  SEQ ID NO: 24 is Pep-17
  SEQ ID NO: 25 is Pep-18
  SEQ ID NO: 26 is Pep-19

SEQ ID NO: 6 is Pep-20
SEQ ID NO: 27 is Pep-21
SEQ ID NO: 28 is Pep-22
SEQ ID NO: 29 is Pep-23
SEQ ID NO: 30 is Pep-24
SEQ ID NO: 31 is Pep-25
SEQ ID NO: 32 is Pep-26
SEQ ID NO: 33 is Pep-27
SEQ ID NO: 34 is Pep-28
SEQ ID NO: 35 is Pep-29
SEQ ID NO: 36 is Pep-30
SEQ ID NO: 37 is Pep-31
SEQ ID NO: 38 is Pep-32
SEQ ID NO: 39 is Pep-33
SEQ ID NO: 40 is Pep-34
SEQ ID NO: 41 is Pep-44
SEQ ID NO: 42 is Pep-45
SEQ ID NO: 43 is Pep-46
SEQ ID NO: 44 is Pep-47
SEQ ID NO: 45 is Pep-48
SEQ ID NO: 46 is Pep-49
SEQ ID NO: 47 is Pep-50
SEQ ID NO: 48 is Pep-51
SEQ ID NO: 49 is Pep-52
SEQ ID NO: 50 is Pep-53
SEQ ID NO: 51 is Pep-54
SEQ ID NO: 52 is Pep-55
SEQ ID NO: 53 is Pep-56
SEQ ID NO: 54 is Pep-57
SEQ ID NO: 55 is Pep-58
SEQ ID NO: 56 is Pep-59
SEQ ID NO: 57 is Pep-60
SEQ ID NO: 58 is Pep-61
SEQ ID NO: 59 is Pep-62
SEQ ID NO: 60 is Pep-63
SEQ ID NO: 61 is Pep-64
SEQ ID NO: 62 is Pep-65

Optimization of Peptide Substrates for the Sensitive Detection of Type E Botulinum Neurotoxin by the Endopep-MS Assay The purpose of the experiments described herein are to optimize a peptide substrate used in the mass spectrometry-based Endopep-MS assay, for the sensitive detection of type E botulinum neurotoxin (BoNT/E). FIG. 1 shows the sequence of the native protein substrate of BoNT/E, SNAP-25 (top; SEQ ID NO:1) and the scheme of Endopep-MS assay for the detection of BoNTs using a peptide substrate (bottom).

The results described herein demonstrate that the newly developed peptide substrates were considerably improved when compared to the established substrate for BoNT/E detection.

A fast and sensitive mass spectrometry method, Endopep-MS (FIG. 1), has been developed in our laboratory. Based on the proteolytic activity, BoNT serotypes can be determined by MS, detecting the specific cleavage products of peptide substrates representing or mimicking the sequence of the BoNT in vivo targets, SNAP-25 (FIG. 1) or other SNARE proteins. The sequence of SNAP-25 is represented by SEQ ID NO: 1, as shown supra.

As discussed above, the present invention features peptide substrates that are selectively recognized by BoNT/E. In exemplary embodiments, the peptide substrate is represented by SEQ ID NO:3, shown below. The bold and underlined residues are the cleavage site of BoNT/E substrates.

SEQ ID NO: 3
$X_1X_2X_3X_4X_5LX_6GX_7EIDTX_8NRQX_9D\underline{\mathbf{X_{10}I}}X_{11}X_{12}KAX_{13}X_{14}X_{15}$
$X_{16}X_{17}$, wherein:
$X_1$, $X_2$ or $X_3$: W, 1-Nal (1-Naphthylalanine), 2-Nal, F, Y, I, L, Nle (norleucine), A, or any other hydrophobic residue;
$X_4$: A or G;
$X_5$: N, K, A, or G;
$X_6$: No residue, or RHMALDM;
$X_7$: N or Q;
$X_8$: Q, R, K or any other positively charged residue;
$X_9$: I, F, K, or R;
$X_{10}$: R, homoArg, Cit (citrulline) or Orn (ornithine);
$X_{11}$: M or Nle;
$X_{12}$: A, F, G, I;
$X_{13}$: D, K, R or any other positively charged residue;
$X_{14}$: S, K, R or any other positively charged residue;
$X_{15}$: N, K, R or any other positively charged residue;
$X_{16}$: K, R or any other positively charged residue; and
$X_{17}$: R, TR; native or amidated C-terminus.

RHMALDM corresponds to residues 161-167 of SEQ ID NO:1 (SNAP-25).

In other exemplary embodiments, the peptide substrate is represented by SEQ ID NO: 4, shown below.

SEQ ID NO: 4
$(X_0)_m$-(SEQ ID NO: 3)-$(X_{18})_n$, wherein,
m: 0 or 1;
n: 0 or 1;
$X_0$: ARENEMDENLEQVS; and
$X_{18}$: IDEANQRATKMLGSG.

ARENEMDENLEQVS corresponds to residues 141-154 of SEQ ID NO:1.

IDEANQRATKMLGSG corresponds to residues 192-206 of SEQ ID NO:1.

SEQ ID NO:4 is derived based on extensive experiments that show cleavage efficiency of peptides with the native sequence of SNAP-25 (141-206), SNAP-25 (156-206), SNAP-25 (156-190) (see examples section below).

Figure 5:
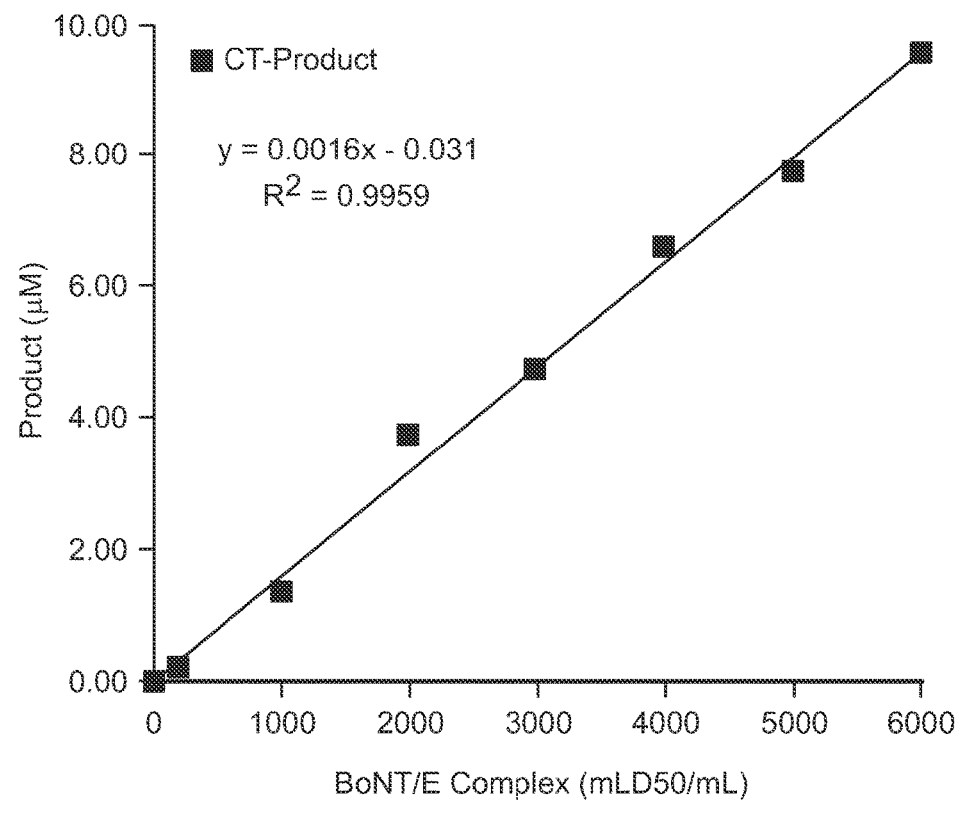

In another set of experiments, the quantitation of the hydrolysis of Peptide#62, shown above, cleaved by BoNT/E spiked in stool and serum matrices was examined. The results are shown in FIG. 5. FIG. 5 shows detection of the cleavage product of the Peptide#62 cleaved by BoNT/E complex spiked in stool matrix (0.5 mL) at various concentrations. Cleavage reaction: 20 uL reaction solution, 37° C. for 30 min. LOD: 0.1 mLD50/mL (e.q. 1 pg/mL) BoNT/E complex (not activated by trypsinization before assay) in serum or stool samples. (Peptide#62, 37° C. for 4 hr).

To further improve the sensitivity of the Endopep-MS assay, experiments were carried out to optimize the current peptide substrate (Pep8, shown below as SEQ ID NO:2) for the detection of BoNT/E. SEQ ID NO:2 corresponds to SNAP-25 positions 156-190 (S. R. Kalb et al. International Journal of Mass Spectrometry (2008), 278, 101-108; b) S. R. Kalb et al. The Botulinum J. (2012), 2(2), 119-134). The BonNT/E cleavage site is highlighted in bold and underlined.

SEQ ID NO: 2
IIGNLRHMALDMGNEIDTQNRQIDRIMEKADSNKT

Pep10, shown in Table 4, and below as SEQ ID NO:5, corresponds to SNAP25 positions 156-186, and has previously been used in the Endopep-MS assay (see U.S. Pat. No. 7,611,856 B2; S. R. Kalb et al. Anal Biochem (2006), 351, 84-92). The BonNT/E cleavage site is highlighted in bold.

SEQ ID NO: 5
IIGNLRHMALDMGNEIDTQNRQIDRIMEKAD products was characterized by MS analysis on an Applied Biosystems 5800 MALDI-TOF/TOF instrument.

Optimal Peptide Substrate of BoNT/E Determined by Truncation, Deletion and Mutation As shown in Table 1 below, extending or truncating either the N- or C-terminal sequence of the current peptide (Pep-8; SEQ ID NO:2) did not generate improved substrates. Table 1 shows relative production of the cleavage product from the hydrolysis of N- and C-terminal truncated peptide substrates by BoNT/E toxins.

TABLE 1

| Peptide | SNAP-25 position | Sequence | CT-product (%) | NT-product (%) |
|---|---|---|---|---|
| Pep-1 | 141-205 | AREMEMDENLEQVSGIIGNLRHMALDMGNEIDTQNRQID<u>RI</u>MEKADSNKTRIDEANQRATKMLGSG | 100 | |
| Pep-2 | 151-206 | EQVSGIIGNLRHMALDMGNEIDTQNRQID<u>RI</u>MEKADSNKTRIDEANQRATKMLGSG | 75 | |
| Pep-3 | 156-206 | IIGNLRHMALDMGNEIDTQNRQID<u>RI</u>MEKADSNKTRIDEANQRATKMLGSG | 89 | |
| Pep-4 | 161-206 | RHMALDMGNEIDTQNRQID<u>RI</u>MEKADSNKTRIDEANQRATKMLGSG | 28 | |
| Pep-5 | 166-206 | DMGNEIDTQNRQID<u>RI</u>MEKADSNKTRIDEANQRATKMLGSG | 19 | |
| Pep-6 | 171-205 | IDTQNRQID<u>RI</u>MEKADSNKTRIDEANQRATKMLGSG | 0 | |
| Pep-7 | 156-205 | IIGNLRHMALDMGNEIDTQNRQID<u>RI</u>MEKADSNKTRIDEANQRATKMLGSG | | 100 |
| Pep-8* | 156-190 | IIGNLRHMALDMGNEIDTQNRQID<u>RI</u>MEKADSNKT | | 100 |
| Pep-9 | 156-188 | IIGNLRHMALDMGNEIDTQNRQID<u>RI</u>MEKADSN | | 81 |
| Pep-10 | 156-186 | IIGNLRHMALDMGNEIDTQNRQID<u>RI</u>MEKAD | | 68 |
| Pep-11 | 156-185 | IIGNLRHMALDMGNEIDTQNRQID<u>RI</u>MEKA | | 77 |
| Pep-12 | 156-184 | IIGNLRHMALDMGNEIDTQNRQID<u>RI</u>MEK | | 58 |
| Pep-13 | 156-183 | IIGNLRHMALDMGNEIDTQNRQID<u>RI</u>ME | | 15 |
| Pep-14 | 156-182 | IIGNLRHMALDMGNEIDTQNRQID<u>RI</u>M | | 10 |

*Pep-8 is the BoNT/E substrate currently used in Endopep-MS assay.
<u>RI</u>: BoNT/E cleavage site.

Investigation of peptide truncation, deletion, single and multiple mutations; resulted in optimal peptides that considerably improve the MS detection sensitivity of the BoNT/E cleavage products.

Peptides were synthesized by a solid phase peptide synthesis method using Fmoc chemistry. Endopep-MS assays were carried out in a 20 mL reaction volume containing peptide substrate, BoNT/E toxins of various concentrations, and other reaction components. For samples in matrix, the toxin was spiked into serum or stool extract, and purified by BoNT specific antibody immobilized on streptavidin beads, followed by an activity assay. MS response of the cleavage Addition of ile at the N-terminal of SEQ ID NO: 2 (Pep-8) slightly increased its hydrolysis rate. C-terminal extension with R or RI improved the detection of CT-product by 20 fold. This is presumably due to elevated ionization efficiency of the cleavage product during mass spectrometry analysis, associated with the incorporation of a positively charged Arg residue. Table 5 below illustrates these results. Table 2 shows relative production of the N- or C-terminal product cleaved from truncated or modified peptide substrates by BoNT/E toxin. The bold and italicized red letter indicates the residue not present in the original SNAP-25 sequence.

TABLE 2

| Peptide | Sequence | CT-product (%) | NT-product (%) |
|---|---|---|---|
| Pep-15 | GNLRHMALDMGNEIDTQNRQID<u>RI</u>MEKADSNKT | 60 | |
| Pep-16 | IGNLRHMALDMGNEIDTQNRQID<u>RI</u>MEKADSNKT | 73 | |
| Pep-8 | IIGNLRHMALDMGNEIDTQNRQID<u>RI</u>MEKADSNKT | 100 | |
| Pep-17 | GIIGNLRHMALDMGNEIDTQNRQID<u>RI</u>MEKADSNKT | 81 | |
| Pep-18 | IIIGNLRHMALDMGNEIDTQNRQID<u>RI</u>MEKADSNKT | 123 | |
| Pep-19 | IIIGNLRHMALDMGNEIDTQNRQID<u>RI</u>MEKADSNKTRI | 2460 | 100 |
| Pep-20 | IIIGNLRHMALDMGNEIDTQNRQID<u>RI</u>MEKADSNKTR | 2678 | 117 |
| Pep-18 | IIIGNLRHMALDMGNEIDTQNRQID<u>RI</u>MEKADSNKT | 123 | 130 |
| Pep-21 | IIIGNLRHMALDMGNEIDTQNRQID<u>RI</u>MEKADSN | 24 | 52 |

Italic and bold letter: the residue not present in the original SNAP-25 sequence, or substituted/mutated residue.

Deletion studies revealed that seven internal residues (RHMALDM) within Pep-20 (SEQ ID NO:6) can be removed without significant negative impact on substrate cleavage. It was also found that three N-terminal residues (NKT) can be omitted as long as the Arg residue is retained on the N-terminus. Moreover, shortened peptides will reduce difficulty and cost in preparation.

SEQ ID NO: 6
IIIGNLRHMALDMGNEIDTQNRQIDRIMEKADSNKTR

Table 3, shown below, shows relative production of the N- or C-terminal product cleaved from internally deleted peptides by BoNT/E toxin. The underscore represents the amino acid residues are deleted from the peptide 20 (SEQ ID NO:6).

TABLE 3

Relative production of the N-or C-terminal product cleaved from internally deleted peptides by BoNT/E toxin.

| Peptide | Sequence | CT-product (%) | NT-product (%) |
|---|---|---|---|
| Pep-20 | IIIGNLRHMALDMGNEIDTQNRQID<u>RI</u>MEKADSNKTR | 100 | |
| Pep-22 | IIIGNLRHMALDMGNE_____RQID<u>RI</u>MEKADSNKTR | 6 | |
| Pep-23 | IIIGNLRHMAL_____IDTQNRQID<u>RI</u>MEKADSNKTR | 17 | |
| Pep-24 | IIIGNL_____DMGNEIDTQNRQID<u>RI</u>MEKADSNKTR | 90 | |
| Pep-25 | IIIGN_____DMGNEIDTQNRQID<u>RI</u>MEKADSNKTR | 19 | |
| Pep-26 | IIIG_____DMGNEIDTQNRQID<u>RI</u>MEKADSNKTR | 43 | |
| Pep-27 | III_____DMGNEIDTQNRQID<u>RI</u>MEKADSNKTR | 30 | |
| Pep-28 | IIIGNL_____NEIDTQNRQID<u>RI</u>MEKADSNKTR | 2 | |
| Pep-29 | IIIGNL_____GNEIDTQNRQID<u>RI</u>MEKADSNKTR | 88 | |
| Pep-30 | IIIGNL_____MGNEIDTQNRQID<u>RI</u>MEKADSNKTR | 33 | |
| Pep-31 | IIIGNL____LDMGNEIDTQNRQID<u>RI</u>MEKADSNKTR | 53 | |
| Pep-29 | IIIGNL_____GNEIDTQNRQID<u>RI</u>MEKADSNKTR | 100 | 100 |
| Pep-32 | IIIGNL_____GNEIDTQNRQID<u>RI</u>MEKADSNKR | 133 | 136 |
| Pep-33 | IIIGNL_____GNEIDTQNRQID<u>RI</u>MEKADSNR | 104 | 84 |
| Pep-34 | IIIGNL_____GNEIDTQNRQID<u>RI</u>MEKADSR | 20 | 36 |

Underscore: the amino acid residudues are deleted from the peptide-20.

Further Improvement was Accomplished by Single or Multiple Substitutions/Mutations Next, the effect of single or multiple substitutions/mutations was examined. FIG. 2 is a table (Table 4) that shows the effect of single amino acid mutations on the detection of cleavage product of mutated peptide-32 by BoNT/E. X represents norleucine. FIG. 2 shows cleavage of the peptides with N-terminal hydrophobic residues. $O_1$: 1-Nal.

New peptides were developed as considerably improved substrates for BoNT/E detection using multiple amino acid mutations, introduction of N-terminal hydrophobic cluster and incorporation of unnatural amino acid residues. Table 5, below, shows the effect of multiple mutations. In Table 5, hR: homoarginine; $O_1$: 1-Nal; $O_2$: 2-Nal.

TABLE 5

| Peptide | Sequence | CT-product (%) |
|---|---|---|
| Pep-44 | IIIGNLGNEIDTQNRQID<u>RI</u>MEKAKSNKR | 100 |
| Pep-45 | IIIAKLGNEIDTRNRQID<u>RI</u>MEKADSNKR | 101 |
| Pep-46 | IIIGKLGNEIDTRNRQID<u>RI</u>MEKADSNKR | 103 |
| Pep-47 | IIIAKLGQEIDTRNRQKD<u>RI</u>MEKADSNKR | 152 |
| Pep-48 | IIIAKLGNEIDTQNRQKD<u>RI</u>MAKADSNKR | 122 |
| Pep-49 | IIIAKLGNEIDTRNRQKD<u>RI</u>MAKADSNKR | 137 |
| Pep-50 | IIIAKLGNEIDTRNRQKD<u>RI</u>MEKAKSKKR | 44 |
| Pep-51 | IIIGNLGNEIDTQNRQID<u>RI</u>KAKAKSKKR | 131 |
| Pep-52 | IIIGNLGNEIDTQNRQID<u>RI</u>MAKAKSKKR | 192 |
| Pep-53 | IIIGNLGNEIDTQNRQID<u>RI</u>MEKARRKKR | 128 |
| Pep-54 | IIIGNLGNEIDTQNRQID<u>RI</u>MEKAKRKKR | 132 |
| Pep-55 | IIIGNLGNEIDTQNRQID<u>RI</u>MEKAKKKKR | 134 |
| Pep-56 | IIIGNLGNEIDTQNRQID<u>RI</u>MEKAKSKKR | 123 |
| Pep-57 | IIIGNLGNEIDTQNRQIDh<u>RI</u>MAKAKSKKR | 172 |
| Pep-58 | IIIGNLGNEIDTQNRQIDh<u>RI</u>MAKAKSKKR | 146 |
| Pep-59 | IIIGNLGNEIDTQNRQIDh<u>RI</u>MAKAKSKKRRR | 49 |
| Pep-60 | IIIGNLGNEIDTQNRQIDh<u>RI</u>MAKAKSKKR-NH$_2$ | 165 |
| Pep-61 | WWWGNLGNEIDTQNRQIDh<u>RI</u>MAKAKSKKR-NH$_2$ | 156 |
| Pep-62 | WWWAKLGQEIDTRNRQKDh<u>RI</u>MAKADSNKR-NH$_2$ | 314 |
| Pep-63 | $O_1O_1O_1$AKLGQEIDTRNRQKDh<u>RI</u>MAKADSNKR-NH$_2$ | 302 |
| Pep-64 | $O_2O_2O_2$AKLGQEIDTRNRQKDh<u>RI</u>MAKADSNKR-NH$_2$ | 288 |
| Pep-65 | $O_2O_2O_2$AKLGQEIDTRNRQKDh<u>RI</u>MAhRADSNKR-NH$_2$ | 302 |

X: norleucine; hR: homoarginine; $O_1$: 1-Nal; $O_2$: 2-Nal

Comparison of the Newly Optimized Substrate with the Old Peptide

Table 6, below, shows a comparison of the cleavage of currently used and newly developed peptide substrates by BoNT/E as described herein.

TABLE 6

| Peptide | Toxin Type | Amount (mLD$_{50}$) | CT-product (Peak ratio) | Relative product |
|---|---|---|---|---|
| Pep-8 | unactivated | 100 | 0.40 | 1 |
| Pep-52 | unactivated | 1 | 2.35 | 581 |
| Pep-8 | activated | 0.15 | 1.07 | 1 |
| Pep-52 | activated | 0.0016 | 5.48 | 511 |

CT-product was determined by the peak ratio of the cleavage product versus an internal standard in a mass spectrometry spectrum.

Figure 4:
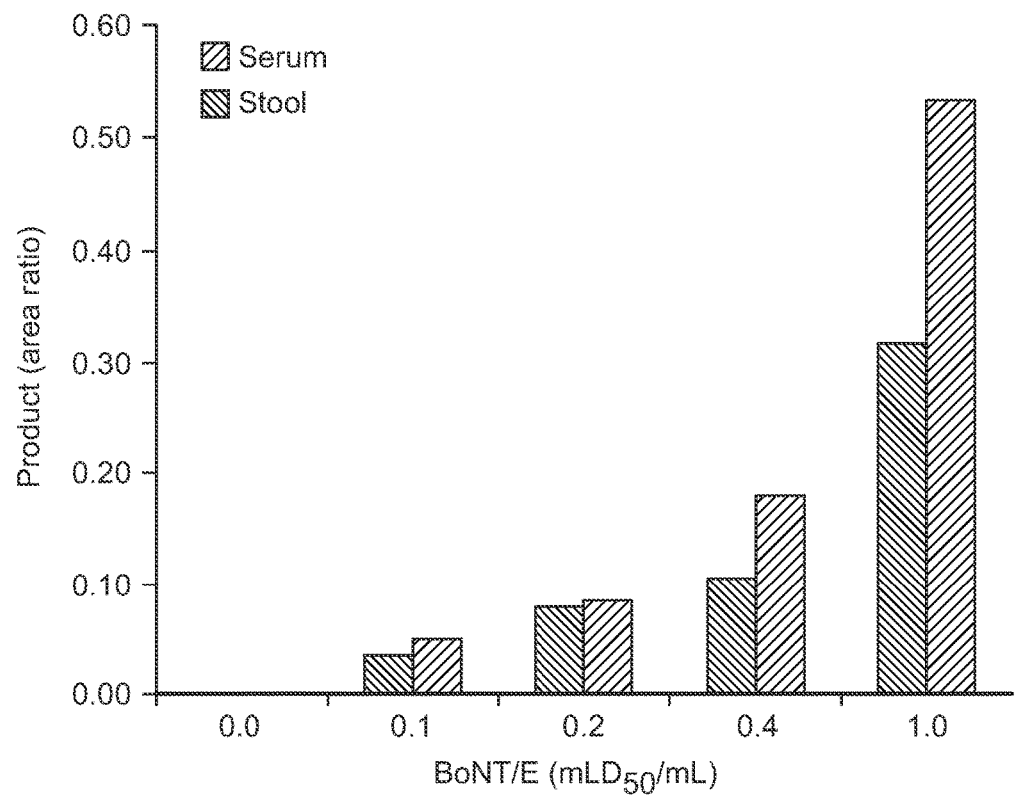

An optimal peptide displayed around a 300-500 fold improvement in the detection of both regular and trypsin activated BoNT/E, for example a 300, 310, 320, 330, 340, 350, 360, 370, 380, 390, 400, 410, 420, 430, 440, 450, 460, 470, 480, 490 or more improvement. Preferably, an optimal peptide displayed around 500-fold improvement on the detection of both regular and trypsin activated BoNT/E toxins. FIG. 4 shows detection of various amounts of BoNT/E spiked in 0.5 mL of serum or stool matrices. An LOD of 0.1 mLD50/mL (1 pg/mL or 5.5 attomole/mL) was achieved by using a new peptide substrate of BoNT/E in biological matrices.

Taken together, the experiments described herein demonstrate optimization of the peptide substrate used in the Endopep-MS assay for the BoNT/E detection by mutation, truncation and deletion studies. New peptide(s) show significant improvement over the currently used substrate. The limit of detection for the toxins in serum, stool and food samples using the new substrate is 0.1 mouseLD$_{50}$/mL, 10-fold lower than that measured by traditional mouse assay.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

What is claimed is:

1. A peptide substrate selectively recognized by BoNT/E comprising the sequence $$X_1X_2X_3X_4X_5LX_6GX_7EIDTX_8NRQX_9DX_{10}IX_{11}X_{12}KAX_{13}X_{14}X_{15}X_{16}X_{17},$$ (SEQ ID NO: 3)

wherein:

$X_1$, $X_2$ or $X_3$: W, 1-Nal (1-Naphthylalanine), 2-Nal, F, Y, I, L, Nle (norleucine), A, or any other hydrophobic amino acid residue;

$X_4$: A or G;

$X_5$: N, K, A, or G;

$X_6$: No residue, or RHMALDM;

$X_7$: N or Q;

$X_8$: Q, R, K or any other positively charged residue;

$X_9$: I, F, K, or R;

$X_{10}$: R, homoArg, Cit (citrulline) or Orn (ornithine);

$X_{11}$: M or Nle;

$X_{12}$: A, F, G, I;

$X_{13}$: D, K, R or any other positively charged residue;

$X_{14}$: S, K, R or any other positively charged residue;

$X_{15}$: N, K, R or any other positively charged residue;

$X_{16}$: K, R or any other positively charged residue; and $X_{17}$: R, TR; native or amidated C-terminus.

2. The peptide substrate of claim 1, wherein RHMALDM corresponds to residues 161-167 of SNAP-25 (SEQ ID NO: 1).

3. A peptide substrate selectively recognized by BoNT/E comprising the sequence $$(X_0)m\text{-}(SEQ\ ID\ NO:\ 3)\text{-}(X_{18})n,$$ (SEQ ID NO: 4)

wherein, m: 0 or 1;

n: 0 or 1;

$X_0$: ARENEMDENLEQVS; and $X_{18}$: IDEANQRATKMLGSG.

4. The peptide substrate of claim 3, wherein ARENEMDENLEQVS corresponds to residues 141-154 of SEQ ID NO: 1.

5. The peptide substrate of claim 3, wherein IDEANQRATKMLGSG corresponds to residues 192-206 of SEQ ID NO: 1.

6. A peptide substrate selectively recognized by BoNT/E comprising IIGNLRHMALDMGNEIDTQNRQIDRIMEKADSNKT (SEQ ID NO:2), wherein SEQ ID NO:2 comprises one or more of the following alterations:

one or more deletions;

one or more mutations; or a combination thereof, wherein at least one of:

amino acid 35 of SEQ ID NO: 2 is R or RT, amino acid 28 of SEQ ID NO: 2 is A, G, F, or I, the deletion comprises the deletion of seven internal residues (RHMALDM), or a combination thereof.

7. A method for detecting the presence of clostridial botulinum neurotoxin serotype E (BoNT/E) in a sample, the method comprising:

a) mixing the sample that may comprise serotype E of clostridial neurotoxins with magnetic beads where specific antibodies against BoNT/E are immobilized to capture toxins;

b) washing toxin-captured beads;

c) transferring toxin-captured beads into a reaction solution that contains the peptide substrate of claim 1 that is selectively recognized by BoNT/E; such that at least a portion of the amount of the substrate is proteolytically cleaved to produce a mixture comprising uncleaved substrate and peptide cleavage products;

d)) analyzing the mixture on a mass spectrometer to produce a signal corresponding to the mass of at least one peptide cleavage product;

e) using the signal corresponding to the peptide cleavage products to identify the presence of clostridial neurotoxin serotype E; and f) quantitating the amount of proteolytic cleavage of the peptide substrate for the clostridial neurotoxin serotype by mass spectrometry using a stable isotope labeled internal standard that has identical sequence to a cleavage product; wherein the amount of active toxin ofBoNT/E in the sample is about 0.05-0.1 pg or more.

8. The method of claim 7, further comprising a control sample.

* * * * *